United States Patent
Parker, Jr. et al.

(10) Patent No.: US 10,271,766 B1
(45) Date of Patent: Apr. 30, 2019

(54) SYSTEMS, DEVICES, AND/OR METHODS FOR MEASURING METABOLIC ENERGY EXPENDITURE

(71) Applicant: Barron Associates, Inc., Charlottesville, VA (US)

(72) Inventors: B. Eugene Parker, Jr., Charlottesville, VA (US); Kevin M. Ehlmann, Charlottesville, VA (US); William T. Gressick, Greenwood, VA (US)

(73) Assignee: Barron Associates, Inc., Charlottesville, VA (US)

( * ) Notice: Subject to any disclaimer, the term of this patent is extended or adjusted under 35 U.S.C. 154(b) by 532 days.

(21) Appl. No.: 15/076,237

(22) Filed: Mar. 21, 2016

Related U.S. Application Data

(60) Provisional application No. 62/135,832, filed on Mar. 20, 2015.

(51) Int. Cl.
| | | |
|---|---|---|
| A61B 5/083 | (2006.01) | |
| A61B 5/097 | (2006.01) | |
| A61B 5/00 | (2006.01) | |
| A61B 5/091 | (2006.01) | |

(52) U.S. Cl.
CPC .......... *A61B 5/0833* (2013.01); *A61B 5/0015* (2013.01); *A61B 5/0836* (2013.01); *A61B 5/091* (2013.01); *A61B 5/097* (2013.01); *A61B 2562/0247* (2013.01); *A61B 2562/0271* (2013.01)

(58) Field of Classification Search
None
See application file for complete search history.

(56) References Cited

U.S. PATENT DOCUMENTS

| | | | | |
|---|---|---|---|---|
| 3,670,726 A | * | 6/1972 | Mahon | A61M 16/08 128/204.18 |
| 4,197,857 A | | 4/1980 | Osborn | |
| 5,072,737 A | * | 12/1991 | Goulding | A61B 5/083 128/204.23 |
| 5,261,415 A | * | 11/1993 | Dussault | A61B 5/0836 250/339.13 |
| 5,664,560 A | * | 9/1997 | Merrick | A61M 16/12 128/203.25 |
| 5,705,735 A | | 1/1998 | Acorn | |
| 6,475,158 B1 | * | 11/2002 | Orr | A61B 5/024 600/529 |
| 6,572,561 B2 | | 6/2003 | Mault | |

(Continued)

OTHER PUBLICATIONS

Matarese, Laura E. "Indirect calorimetry: technical aspects." Journal of the American Dietetic Association 97.10 (1997): S154-S160.*

*Primary Examiner* — Patricia Mallari
*Assistant Examiner* — Jairo H Portillo
(74) *Attorney, Agent, or Firm* — Michael Haynes PLC; Michael N. Haynes

(57) ABSTRACT

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, facilitating determination of the oxygen consumption, carbon dioxide production, respiratory exchange ratio, and/or energy expenditure of a mammal.

4 Claims, 8 Drawing Sheets

(56) References Cited

U.S. PATENT DOCUMENTS

| | | | |
|---|---|---|---|
| 6,884,222 B1 | 4/2005 | Braig | |
| 6,899,684 B2 | 5/2005 | Mault | |
| 6,942,623 B2 | 9/2005 | Robergs | |
| 7,044,911 B2 | 5/2006 | Drinan | |
| 7,357,776 B2 | 4/2008 | Nishibayashi | |
| 8,690,769 B2 | 4/2014 | Edman | |
| 8,852,097 B2 | 10/2014 | Shimada | |
| 9,089,285 B2 | 7/2015 | Lee | |
| 2004/0013817 A1* | 1/2004 | Mizutani | H01L 21/02137 427/569 |
| 2004/0143297 A1* | 7/2004 | Ramsey, III | A61N 1/3975 607/5 |
| 2005/0143635 A1* | 6/2005 | Kamath | A61B 5/14532 600/347 |
| 2006/0201503 A1* | 9/2006 | Breen | A61M 16/08 128/204.18 |
| 2006/0229526 A1* | 10/2006 | Chen | A61B 5/083 600/532 |
| 2007/0107728 A1* | 5/2007 | Ricciardelli | A61B 5/087 128/204.21 |
| 2009/0084126 A1* | 4/2009 | Schartel | C01B 13/0214 62/260 |
| 2009/0227887 A1* | 9/2009 | Howard | A61B 5/0833 600/531 |
| 2010/0298734 A1* | 11/2010 | Colman | A61B 5/083 600/543 |
| 2013/0291869 A1* | 11/2013 | Daly | A61M 16/0045 128/204.23 |
| 2015/0032019 A1* | 1/2015 | Acker | A61B 5/082 600/532 |

\* cited by examiner

SYSTEMS, DEVICES, AND/OR METHODS FOR MEASURING METABOLIC ENERGY EXPENDITURE

CROSS-REFERENCES TO RELATED APPLICATIONS

This application claims priority to, and incorporates by reference herein in its entirety, U.S. Provisional Patent Application 62/135,832, filed 20 Mar. 2015.

BRIEF DESCRIPTION OF THE DRAWINGS

A wide variety of potential, feasible, and/or useful embodiments will be more readily understood through the herein-provided, non-limiting, non-exhaustive description of certain exemplary embodiments, with reference to the accompanying exemplary drawings in which.

DESCRIPTION

Figure 1:
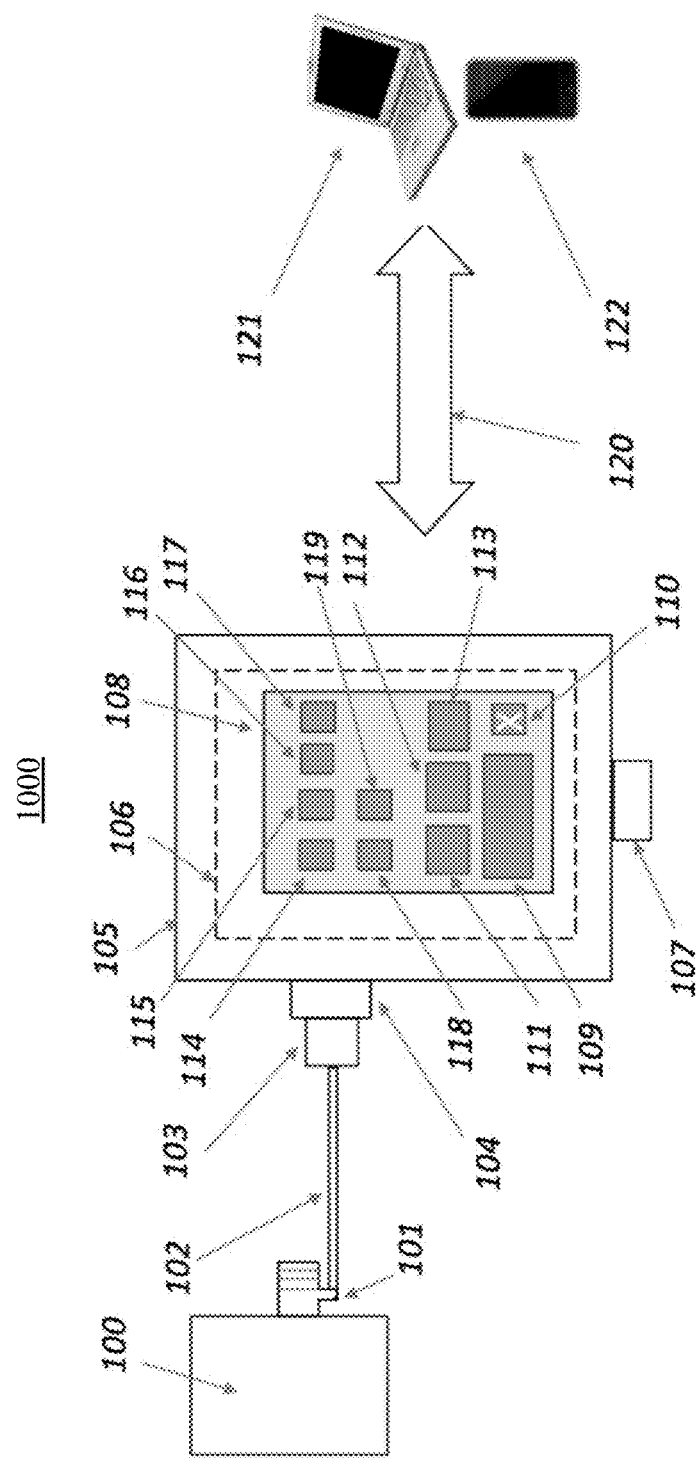
FIG. 1 is a block diagram an exemplary embodiment of a system.

During aerobic respiration, energy expenditure (EE) can be quantified by measuring oxygen uptake, $\dot{V}_{O2}$, and carbon dioxide production, $\dot{V}_{CO2}$. That is, by measuring the net oxygen ($O_2$) used and the net carbon dioxide ($CO_2$) produced by the body while an individual is performing any activity, e.g., sitting, standing, walking, running, gardening, etc., the energy cost of the activity can be determined. This process of indirect calorimetry (IC) can provide accurate and reliable measurement of metabolic gas exchange.

EE can be vital in many fields. Exercise physiologists, for example, often need to measure the EE associated with different physical activities and intensity levels, to quantify non-exercise activity thermogenesis, and to investigate the pathogenesis of obesity and diabetes. The respiratory exchange ratio (R) can be used to study differences in individuals' metabolic responses to nutrient ingestion and is expressed as:

$$R = \dot{V}_{CO2}/\dot{V}_{O2}$$

Engineers commonly need to evaluate the energetics and metabolic efficiency of new products, e.g., walkers and crutches. Clinically, measures of $\dot{V}_{O2}$ and $\dot{V}_{CO2}$ can be key to diagnosing and/or managing patients with impaired cardiorespiratory function, performing cardiac catheterization-based assessment of the severity of heart failure, pulmonary arterial hypertension, and valvular heart disease, understanding acute illness, and/or assessing enteral and parenteral nutrition. For example, the gold standard for clinically measuring cardiac output based on the Fick Principle is often not used in practice due to the complexity of measuring $\dot{V}_{O2}$. Instead, equation-based estimates are typically used in place of direct measurement despite the substantial error introduced and its associated clinical consequences.

Similarly, knowledge of the resting metabolic rate (RMR) of acutely ill and critically ill hospital patients can be helpful to assessing their energy intake (EI) needs, but typically is not adequately addressed. That is, the predictive equations that are commonly used to determine patients' EI needs are clinically inaccurate in approximately 25% of patients. Nutritionists use EE to evaluate the likelihood of over- and under-nutrition, as well as R to gauge dietary adherence to low-carbohydrate or low-fat diets. Anthropologists rely on R measures to assess the EE and diets of subsistence-level populations.

The focus herein is on the development and validation of a novel, cost effective, and/or portable device for accurately and reliably measuring $\dot{V}_{O2}$, $\dot{V}_{CO2}$, and R in humans and other mammals.

The "one-button" (turnkey) operation of the proposed Mobile Metabolic Measurement (M3) system can make it practical and/or affordable for use by non-experts in hospital, laboratory, field, and/or home settings. Based on its unique combination of mobility, ease of use, low cost, and/or high accuracy, the M3 system can have a significant and sustained impact on metabolic assessment across numerous fields.

The M3 can use proven, stable, and/or reliable $O_2$ and $CO_2$ sensors that can integrate measurement of relative humidity (RH), temperature, and/or barometric pressure to achieve the targeted high accuracy system. The M3's sensors can offer maintenance-free operation (e.g., self-calibrating in air) and/or on-board self-diagnostics. The proposed approach can be compatible with future (e.g., nanotechnology) sensor upgrades. The M3 need not use a flowmeter, as flowmeters are expensive, require calibration, and are the biggest source of $\dot{V}_{O2}$ and $\dot{V}_{CO2}$ estimation error. Similarly, the M3 need not be used at sea level or in any assumed fractional mixes of $O_2$, $CO_2$, or other gases, so that it can be used in studies at higher altitudes, such as mountain climbing and/or cycling exercises, and/or studies of respiratory responses to elevated $CO_2$ levels, to cite just a few examples.

The M3 system can completely obviate the need for a flowmeter and/or can find clinical and research application wherever low cost, ease of use, and/or high accuracy is a priority.

As shown in FIG. 1, an exemplary embodiment 1000 of the M3 system can include a standard face mask 100 applied over a subject's face to channel and/or direct exhalations of the subject. When the subject is instead using a mouthpiece, rather than a mask, the subject's nose can be sealed, such as via a nose clip, to prevent a substantial portion of their exhalations from evading sampling by the M3 system. Connected to mask 100 can be a sampler or flow tube 101, which can sample from approximately 0.1% to approximately 10 percent of the subject's total exhalation volume. Fluidically connected to flow tube 101 can be a flexible moisture managing conduit 102 that is formed from a highly selective, semi-permeable membrane to water vapor (such as a tube or tubes formed from Nafion®, which is available from DuPont), which can use a combiner adapter at each end if one or more tubes are paralleled. In line or at an end of conduit(s) 102 can be a flow control valve 103, such as a manually operated Hans Rudolph model 2130 three-way directional stopcock, which can allow a subject to control when and/or to what extent their exhalations are sampled. Fluidically coupled to conduit 102 and/or control valve 103 can be a check valve and/or one-way valve 104, such as the Hans Rudolph 1230 one-way valve, that can be configured to substantially impede and/or prevent reversal of flow (i.e., keep a sample flowing from the flow tube 101 toward the flow control valve 103 only). Conduit 102, control valve 103, and/or one-way valve 104 can be fluidically coupled to a sealable mixing tank 105, which can have an access door or top lid 106 that is configured with seals and/or a latch. Connected to tank 105 can be an exhaust valve 107, which can be a one-way valve and/or can be positioned at a right angle to an inlet to tank 105, and thereby can encourage thorough mixing of the samples to form a substantially homogeneous gas within the tank. Exhaust valve 107, which can be a Hans Rudolph 1230 one-way valve, can be configured to maintain approximately 1 atmosphere of pressure within mixing tank 105 at sea level, or whatever the ambient pressure may be when used at a different altitude or condition. Located inside tank 105 can be a specialized tank information device 108, which can comprise electronic components such as a power supply, A/D converter configured for digitizing sensed data, microprocessor for processing sensed data, an I/O device such as a display (e.g., active, passive, LED, EL, OLED, LCD, FED, SED, PDP, cathodoluminescent, electroluminescent, photoluminescent, incandescent, electrophoretic, electrochromic, electrowetting, electromechanical modulative, resistive touchscreen, capacitive touchscreen, and/or inductive touchscreen, etc.) for rendering sensed, processed data, and/or remotely provided information and/or commands, and/or a transceiver configured for transmitting sensed data and/or receiving commands from a distant controller. Located inside tank 105 can be a battery 109, which can provide power for the sensors and/or electronic components inside tank 105. Located inside or outside tank 105 can be a power switch 110, which can disrupt and/or restore electrical power flow between battery 109 and information device 108. In certain exemplary embodiments, information device 108 can include a special purpose processor 112 that is specially configured to process sensor data, a memory 112 for storing data and/or commands, a display, a wireless telemetry module 113, such as e.g., a Bluetooth transceiver. Within tank 105 and/or comprised by information device 108 can be an oxygen ($O_2$) sensor 114, a carbon dioxide ($CO_2$) sensor 115, a barometric pressure sensor 116 (which can be integrated into oxygen sensor 114), a temperature (T) sensor 117 (which can be integrated into carbon dioxide sensor 115), a relative humidity (RH) sensor 118 (which can be integrated into carbon dioxide sensor 115), one or more other optional sensors 119, and/or a wireless link 120 that is configured to transmit sensor data such as measurements. When implemented via Bluetooth, wireless link 120 can be operated at approximately 2.4 GHz. Wirelessly coupled to wireless telemetry module 113 can be an external information device, such as a computer 121 and/or a smart phone 122, that is specially configured to run indirect calorimetry software and/or display results of measurements and/or computations.

Figures 2A, 2B, 2C:
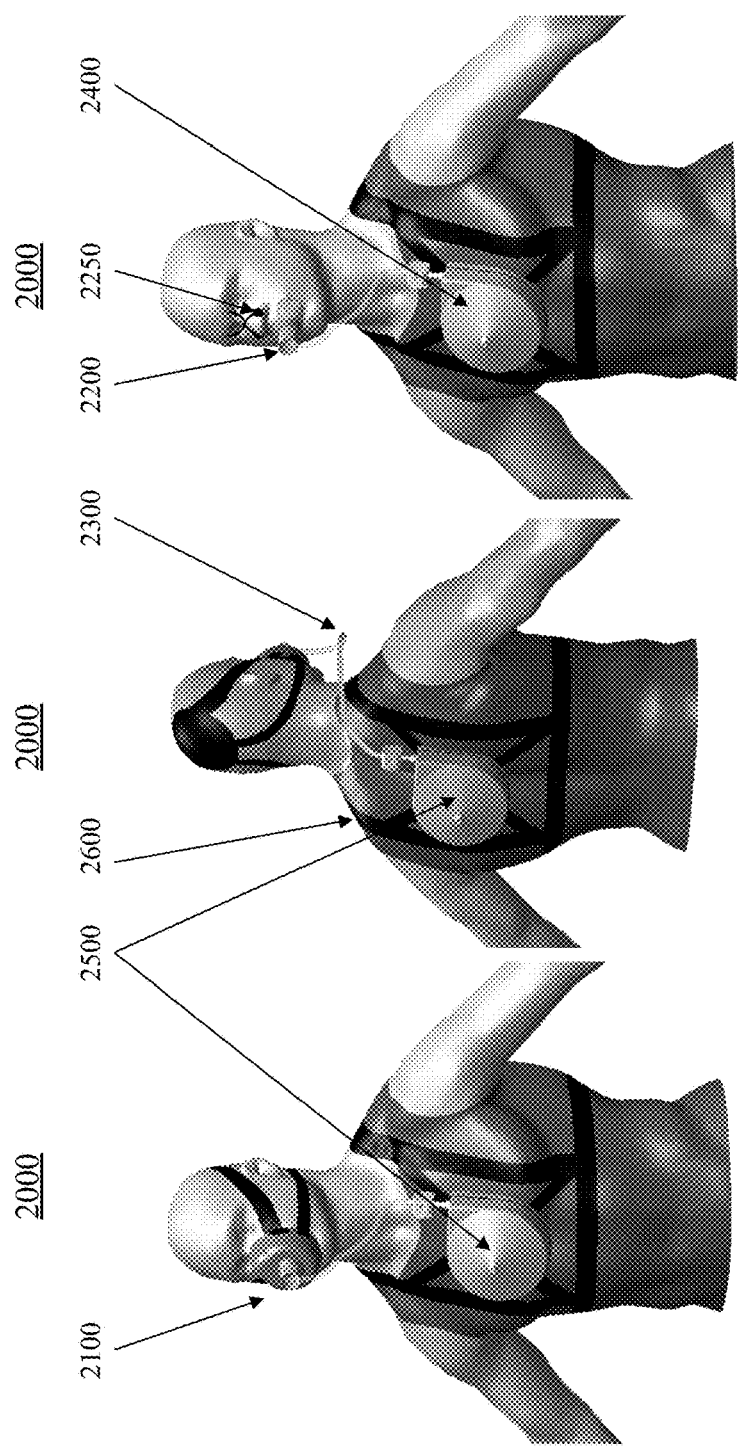
FIGS. 2A, 2B, and 2C are illustrations of exemplary embodiments of a system.

FIGS. 2A, 2B, and 2C illustrate various implementations of the M3 system 2000. Exhalations, or samples thereof, can be "captured" via facemask 2100, which can be a standard ventilation face mask that couples to facial contours to prevent gas leakage, and/or a standard mouthpiece 2200 with nose clip 2250, and routed via moisture managing conduit 2300 to a user operable flow control valve 2400 to sensors contained in and/or attached to tank 2500. Harness 2600 can be reversible, enabling tank 2500 to be worn on the chest (FIG. 2A) or back (FIG. 2B). Tank 2500 can rest beside and/or on exercise equipment (e.g., treadmill).

Figure 8:
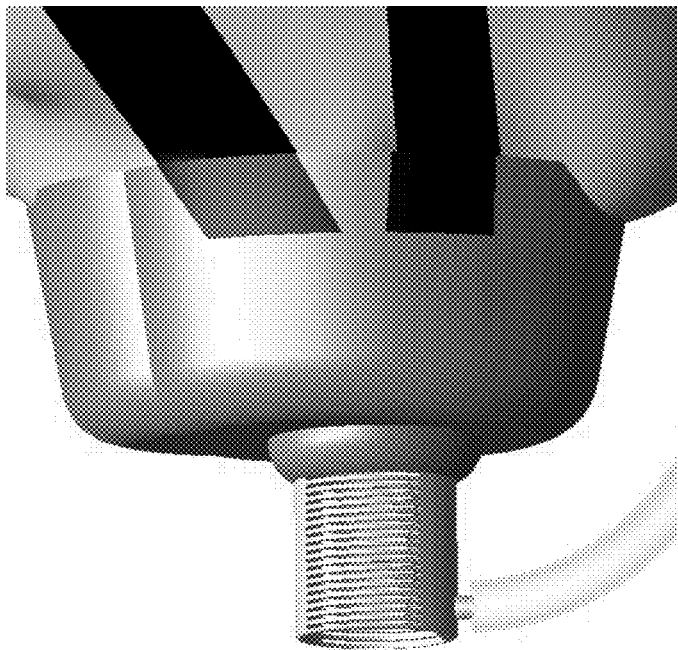
FIG. 8 is illustration of an exemplary embodiment of a system.

FIG. 8 illustrates an exemplary embodiment of a face mask along with a flowtube and conduit.

Figure 9:
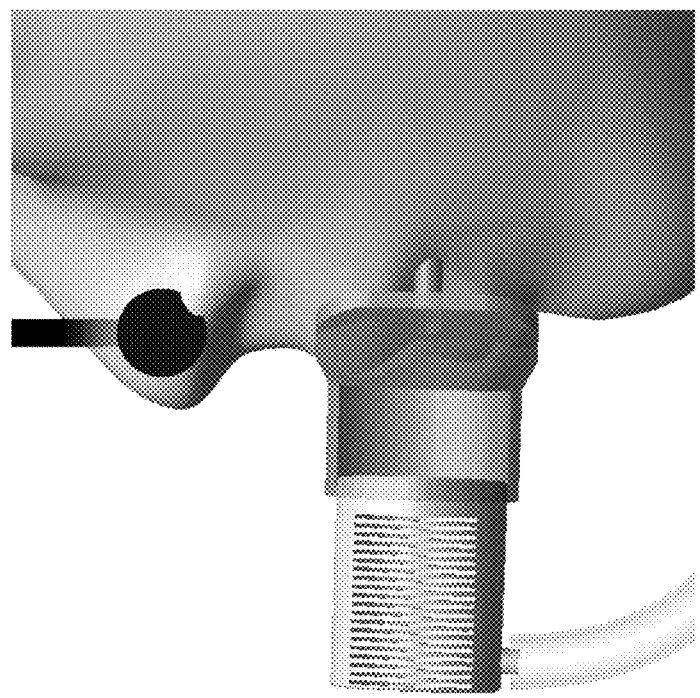
FIG. 9 is illustration of an exemplary embodiment of a system.

FIG. 9 illustrates an exemplary embodiment of a mouthpiece and nose clip, along with a flowtube and conduit.

Figures 3A, 3B:
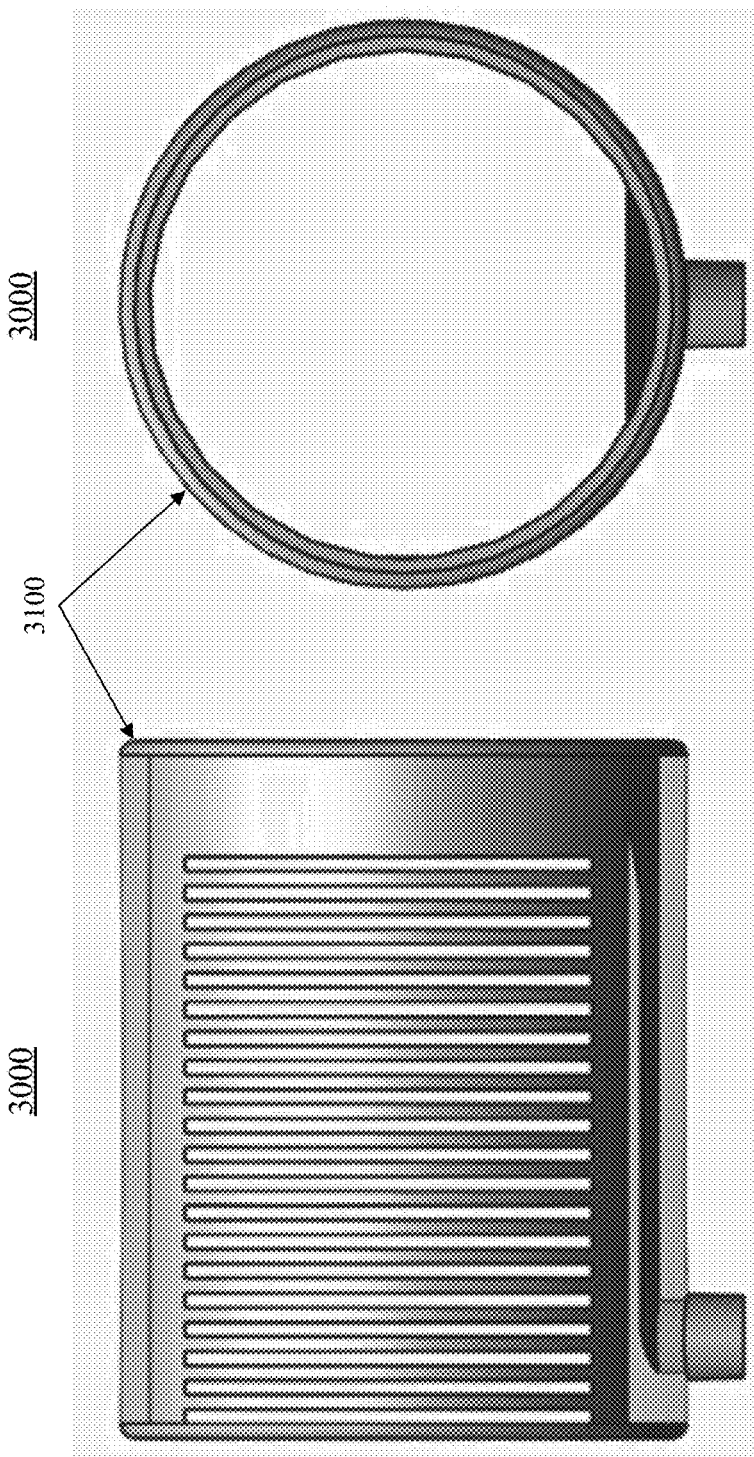
FIG. 3A is side view of an exemplary embodiment of a device.
FIG. 3B is an end view of an exemplary embodiment of a device.

An innovative flow tube 3000 specifically designed for this application is shown in FIGS. 3A (side view) and 3B (end view), which shows the flow tube walls 3100, channel 3200, and outlet port 3300. Flow tube 3000 can connect to the face mask (or mouthpiece) and/or can direct a small fraction of exhalations (e.g., 0.1% to 10%, including each and every value and subrange within that range, such as 1.03%), although the precise amount is not necessarily critical and need not affect the M3's accuracy) into a lightweight, chest- or back-worn mixing tank, the volume of which is not critical (e.g., 1 Liter would be adequate and would enable mobility) (FIG. 4), such as via a short length of flexible moisture managing conduit, which can remove water vapor. The percentage of exhalations diverted into the mixing tank can be controlled via the design of the flow tube 3000 and/or by the design of valve 4200, which can be a rotary valve or a three-way stopcock that enables either on/off or continuous control of the flow through the rotary valve 4200. Note that the version of flow tube 3000 that is configured for use with a mechanical ventilator can eliminate the vertical air slots 3400.

Figure 4:
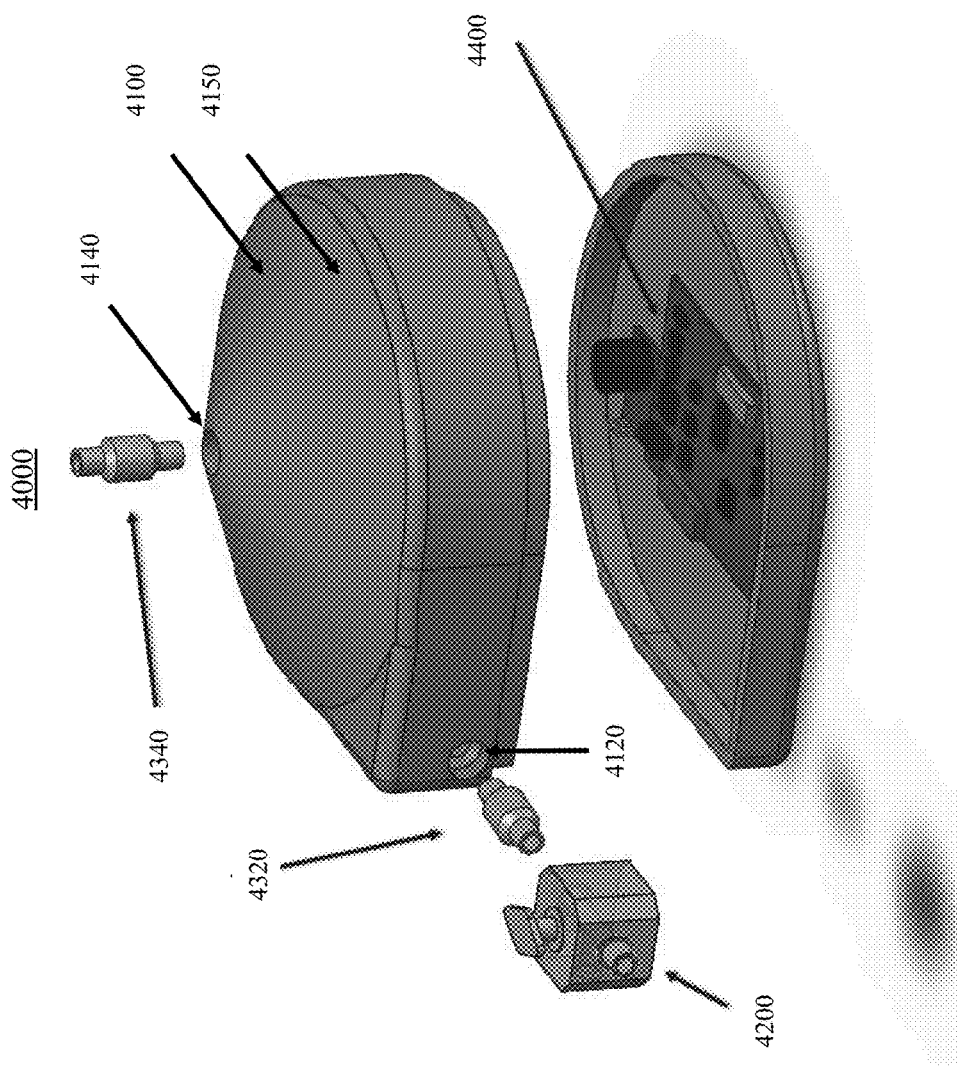
FIG. 4 is illustration of an exemplary embodiment of a system.

As shown in FIG. 4, mixing tank 4100 can have a valve 4200 that can connect directly to a one-way inlet valve 4320 on inlet port 4120 of tank 4100. Actuation of valve 4200 can enable the desired approximate fraction of exhalations to enter tank 4100. The tank can have a one-way outlet valve 4340 located at the outlet port 4140 on the center of its face to allow the release of homogeneous tank gases, helping to ensure that the pressure in tank 4100 remains substantially atmospheric.

Inside the tank can be electronic components 4400, which can form an information device and/or include a microcontroller, I/O device such as a display, Bluetooth transceiver, $O_2$ sensor, $CO_2$ sensor, barometric pressure sensor, temperature sensor, relative humidity (RH) sensor, and/or compact battery.

To operate the M3 system, the user can open lid 4150 of self-sealing tank 4100 (which will flush tank 4100 with fresh air), flip a switch that powers on the electronics, and close tank lid 4150. The microcontroller can receive, display, cause to be transmitted, and/or cause to be displayed, data and/or information, such as sensor data, processed data, analytical information, commands, and/or instructions, etc.). For example, the microcontroller can be programmed to immediately establish a Bluetooth pairing with an information device, such as a PC or smartphone and, once paired, can begin reading, storing in nonvolatile memory, and/or wirelessly transmitting tank sensor data, such as at a rate of approximately 20 Hz. Initial sensor data transmitted by the microcontroller can correspond to atmospheric values. The time of first detection of an increase in tank volumetric $CO_2$ fraction above a pre-designated threshold value $\varepsilon_{FT,CO2}$ and/or decrease in tank volumetric in $O_2$ fraction below a pre-designated threshold value $\varepsilon_{FT,O2}$ can indicate the start of the M3 measurement period and/or the information device can sound an audible tone. Upon achievement of a near steady state in tank volumetric $O_2$ fraction (i.e., $F_{T,O2}$) deviations falling below a threshold amount, $\varepsilon_{FT,O2}$, and/or achievement of a near steady state in tank volumetric $CO_2$ fraction (i.e., $F_{T,CO2}$) deviations falling below a threshold amount, $\varepsilon_{FT,CO2}$), and/or after a pre-designated time interval, data collection can terminate and the information device can again sound a tone. Following data collection, the information device can display the computed $\dot{V}_{O2}$, $\dot{V}_{CO2}$, and R values.

Figures 5A, 5B, 5C:
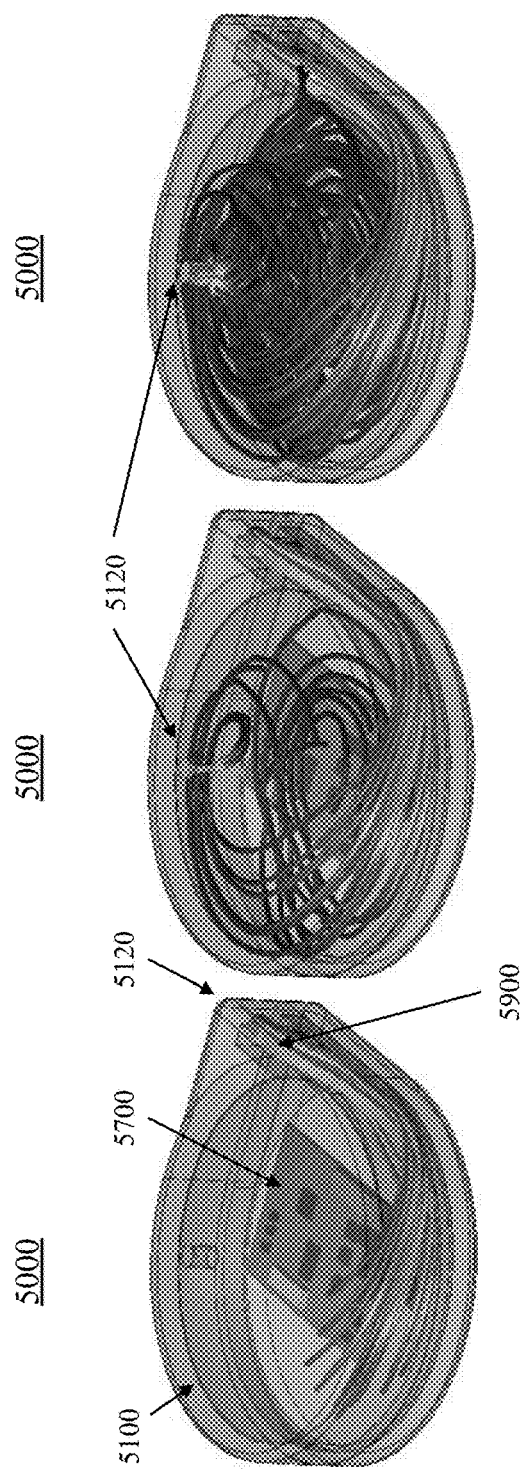
FIGS. 5A, 5B, and 5C are illustrations of exemplary fluid flows.

As shown in FIG. 5A, a first exhalation flow 5900 can enter tank 5100 through inlet port 5120 on the side of tank 5100. As shown in FIG. 5B, the incoming flow continuing to rotate as it works its way towards the exit port 5140 on the top face of tank 5100, mixing the expiratory flow with the extant tank gas and circulating it across the sensors located on the PCBs 5700 at the bottom of the tank. FIG. 5C shows the fully developed flow.

The M3 system can offer an unparalleled combination of low cost, ease of use, accuracy, and/or mobility for making metabolic measurements in clinical, research, field, business, and/or home settings. The system can offer "one-button" turnkey operation because no expertise need be required to set up and/or use the system. There need be no onerous gas sensor and/or flowmeter calibration requirements. The M3 system can employ a factory-calibrated $O_2$ sensor and/or a self-calibrating (in air) $CO_2$ sensor. The M3 system can completely eliminate the requirement for a flowmeter. The M3 system can typically be used over a period of ≤20 min (corresponding to resting/exercise minute ventilations, $\dot{V}_E$s, spanning approximately 5-200 L/min). The use of user-selectable exhalation fraction selections (e.g., approximately 1%, approximately 0.5%, etc.) can enable the operation period to be optimized for different expected $\dot{V}_E$s. The M3 system can be used for metabolic steady state operation, by far the most common type of application. The metabolic steady-state assumption is shown in the Theory of Operation section (below) to obviate the need for a flowmeter to measure minute expirations (i.e., $\dot{V}_E(t)$), as well as for additional sensors to measure the expiratory fractions of $O_2$ (i.e., $F_{E,O2}$) and $CO_2$ (i.e., $F_{E,CO2}$).

Mouthpiece

To acquire its measures, the M3 system can be designed to work with any brand face ventilation mask or mouthpiece with nose clip. The flow tube can be used as a mouthpiece or a separate mouthpiece can be attached to the flow tube, and can be used to connect the M3 flow tube to a metabolic simulator, human subject, and/or other mammal; and thus the possibility of mask leakage can be very low to zero.

Flow Tube

The novel flow tube design, depicted in FIG. 3A, can minimize dead space while diverting a specified small fraction (defined by flow tube design) of exhalations (e.g., ~1% of the volumetric flow) into the mixing tank; the exact fraction is not critical and need have no effect on $\dot{V}_{O2}$ and $\dot{V}_{CO2}$ estimation accuracy. The effect of flow into the diverting tube can limit the duration over which $\dot{V}_{O2}$ and $\dot{V}_{CO2}$ measurements are obtained. The actual amount of flow need not affect $\dot{V}_{O2}$ and $\dot{V}_{CO2}$ measurement accuracy, which can be an advantage over conventional indirect calorimetry systems. The one-way, inlet port tank valve depicted in FIG. 4 as 4320 can substantially ensure that gas from the tank is not inhaled.

In FIG. 3A can be seen a thin, reed-like closed-end channel at the bottom of the flow tube that can be used to divert a small fraction of exhaled gas to an exit port at the distal bottom of the mouthpiece, and thereby into the tank (via the user-actuated control valve (e.g., three-way stopcock) and a one-way valve (see FIG. 4). The flow tube channel design can avoid disrupting the laminar gas inflow and/or can divert a fraction of expired gas into the tank when the user-actuated control valve (e.g., three-way stopcock) near the inlet port is open (see FIG. 4). Both the proximal and distal ends of the flow tube can be open to the atmosphere. The flow tube in FIG. 3A can have slots cut along, and/or perpendicular to, its longitudinal axis downstream of the bottom channel opening. Unlike conventional two-way and three-way valves attached to the facemask or mouthpiece, the open-slotted design of the flow tube need not introduce dead space, re-breathing issues, or significant breathing resistance, since the main body of the flow tube can be open to the atmosphere (mechanically-ventilated patients can use an unslotted version of the design). The slots need not affect the gas entering the tank, as they can be located downstream of the channel that connects to the tank. By allowing only a fraction of exhalations into the tank, a relatively small tank can be used, enabling the M3 system to be mobile. Larger tank sizes can also be used to increase test duration. A user guide can relate test duration to fractional flow and $\dot{V}_E$.

For example, diverting approximately 1% of exhalations into the tank can result in a value for the time constant $\tau=V_T/\dot{V}_E$ that is on the order of minutes for $\dot{V}_E \leq 200$ L/min (for resting adults, approximately $5 \leq \dot{V}_E \leq 10$ L/min)).

Tank

The tank can be designed to take advantage of the momentum of exhalations to establish homogenous mixing. An exploded view diagram of the tank is given in FIG. 4. The hollow, lightweight tank, which, like the flow tube, can be fabricated out of non-conductive plastic to enable Bluetooth signal transparency, can have a removable lid that can be opened to flush the tank with ambient air, and/or to enable activation/deactivation of the M3 system's electronics. A rubber gasket running around the edge of the tank lid can ensure a gas-tight seal. The battery and pylon-mounted motherboard and/or sensor printed circuit boards (PCBs) can be located on the bottom of the tank, which can allow easy access when the lid is removed. Placing the inlet and outlet ports at right angles to one another can avoid creating a direct streamline between the two ports and/or forces the inflowing expirations to mix homogeneously with gas in the tank. Numerically solving the Navier-Stokes equations describing the motion of the fluid in the tank (e.g., via the computational fluid dynamics software package, SolidWorks FloXpress) can yield the simulation results shown in FIG. 5C, illustrating homogenous mixing even at the lowest expected flow rate. The flow rate used in this simulation is 5 L/minute; for normal resting adults the range is approximately $5 \leq \dot{V}_E \leq 10$ L/minute.

User-Actuated Control Valve

A user-actuated control valve that connects directly or via a moisture management conduit to the tank inlet valve, as shown in FIG. 4, can be used to initiate an M3 system measurement session. This can be accomplished using a Hans Rudolph 2130 (three-way, T-shape) Manual Directional Control Stopcock. After the test subject has reached a nominal steady state in her/his EE rate (i.e., metabolic equivalent or MET level), which typically requires ~3 min for EEs below her/his ventilatory threshold, the control valve lever can be rotated from the 'OFF' to an 'ON' position. Smaller fractional flows into the tank (e.g., based on the selected flow tube) can enable longer test durations and/or accommodation of higher $\dot{V}E$ values (e.g., t values on the order of minutes for approximately $100 \leq \dot{V}_E \leq 200$ L/min); most non-athletes cannot sustain $\dot{V}_E \geq 100$ L/min for ≥1 min.

Tank Inlet and Outlet Valves

Two one-way Hans Rudolph 1230 Series one-way valves can attach directly to the tank, as shown in FIG. 3. This valve need not be dependent on gravity, can be very sensitive to low flow, and/or can have excellent non-sticking characteristics. Tapered valve ports can enable secure attachment to the tank and/or allow the valve to be removed easily for cleaning.

Microcontroller

The M3 motherboard can include a Texas Instruments MSP430FR5869 16 MHz ultra-low power microcontroller with 64 KB of combined Flash and/or RAM memory and 2 KB of SRAM. The microcontroller can have multiple timers, a 12-bit analog-to-digital converter (ADC), sample and-hold registers that can service 16 external input channels, and/or multiple high-speed serial communication controllers (potentially including SPI and/or $I^2C$ busses). Sensor data can be sampled, for example, at an approximately 20 Hz rate. In-tank condensation need not be an issue since the moisture management conduit used to transport saturated user exhalations to the tank can remove the excess moisture.

Wireless Transceiver

The M3 motherboard can include a BlueGiga WT12 integrated Bluetooth module designed for low-power RF applications. This class 2 Bluetooth module, which can contain an antenna and/or a fully implemented protocol stack, can enable online transfer of sensor data to Bluetooth capable devices at ranges of up to 40 m.

$O_2$/Barometric Pressure Sensor

A $CO_2$Meter UV Flux 25% Oxygen Sensor with integrated barometric pressure sensor can be used. The $F_{T,O2}$ measurement range is 0-25%, with a worst-case accuracy of ±0.5% (i.e., ±2% of the 0-25% range) and a diffusion response time of <30 s. The pressure sensor worst-case accuracy is ±0.5 kPa over 50-120 kPa (1 atm=101.3 kPa). The microcontroller interface can be via a serial controller.

As another example, an SST Sensing O2S-FR-T3 Miniature Oxygen Sensor with an OXY-LC Oxygen Sensor Interface integrated barometric pressure sensor can be used to measure the tank $O_2$ volumetric fraction. The sensor measurement range is 0-25%, with an error of 0.5%. This sensor has a response time of ≤4 s. The microcontroller interface can be via a RS485 serial controller.

$CO_2$/Temp/RH Sensor

A K-33 BLG 30% $CO_2$/Temp/RH Sensor from $CO_2$Meter can be used in the M3 system. It has a measurement range for $F_{T,CO2}$ of 0-30%, a worst-case accuracy of ±0.9% (i.e., ±3% of the 0-30% range), and a diffusion response time <25 s. The temperature measurement range is −40 degrees C. to +65 degrees C., accurate to ±0.4 degrees C. (at 25 C). The relative humidity (RH) measurement range is 0 to 100% (non-condensing), accurate to ±3%. The interface with the microcontroller can be via the $I^2C$ digital bus.

As another example, a CO2S-W Wide Range Ultra Low Power CO2/Temp/RH Sensor can be used to measure the tank $CO_2$ volumetric fraction. The sensor measurement range is 0-20% $CO_2$, accuracy is ±5%, and response time of ≤4 s. The RH sensor is accurate to ±3% RH over the range 20-55 degrees C. The microcontroller interface can be via RS232.

Conduit

One or more 12-in (front worn) or 18-in (back worn) lengths of conduit, such as a moisture managing conduit that is formed from a highly selective, membrane that is semipermeable to water vapor, such as Nafion® tubing, can be used to connect the flow tube to the user-actuated control valve. Both lengths of conduit can be sufficient to bring the relative humidity and/or water vapor pressure of breath exhalations to equal that of ambient air, thereby substantially drying exhalations and/or substantially eliminating exposure of the $O_2$ and/or $CO_2$ sensors to water vapor and/or condensation. As water vapor in breath exhalations travels through tubing, it can be absorbed into the tubing and evaporate into the surrounding air; up to 100% of $O_2$ and $CO_2$ exhalations can be retained in the tubing. Each end of the tubing can be attached to a 3D-printed (sterolithography) fitting.

The conduit that can connect the flow tube to the user-controlled valve (stopcock) can passively dry the saturated exhalations flowing through the tubing, although regular tubing potentially can be used when condensation is unlikely to form or build up on the sensors in the tank. The conduit can be comprised of multiple lines to get the volume of flow needed into the tank without substantial resistance. These individual lines can be unbound (i.e., not bound together, so that they can be loose and free), so that each can have full exposure to the atmosphere to facilitate drying of the transported exhalations. Each tubing end can be attached to a connector (which can be 3D-printed) that can accommodate the necessary input/output connections from the flow tube to the user-controlled valve (stopcock). In certain exemplary embodiments, Nafion® dryers (also called "Gas Sample Dryers") can use multiple Nafion® tubes in parallel and/or a counter current flow of relatively dry gas (e.g., air), so that the drying that occurs can be more efficient (since the lines can be enclosed in a casing that is not open to the atmosphere and/or are in close proximity to one another). The expired air coming out of the tank can be used for this countercurrent flow of dry gas.

Battery

Power can be provided by an UltraLife Batteries Li-Ion 10.8 V, 2.4 AH rechargeable battery (UBBL21), which weighs only 151 g. An Astrodyne DC/DC converter can be used to drop the voltage to approximately 4.0 or 5.0 V to power the $O_2$ and/or $CO_2$ sensors; another Astrodyne converter can be used to drop the voltage to 3.3 V to power the $CO_2$ sensor and/or other components (e.g., microcontroller and transceiver). The battery can power the system for ≥1 hour; the microcontroller can monitor charge status via an ADC and output the status via Bluetooth.

Simulator for Validation

A Vacumed Metabolic Simulator with Mass Flow Controller (Model 17056) can be used to optimize and/or validate the performance of the M3 system. This high-precision device can include a motorized calibration syringe that enables reliable control of tidal volume (TV); selectable TV values are 0.5, 1.0, 1.5, 2.0, 2.5, and 3.0 L to an accuracy of ±0.25% and respiratory rates spanning 6 to 80 breaths/min, resulting in $\dot{V}_E$ values that can range from 3 to 240 L/min. The device can utilize a separate mass flow controller and a calibration gas source, the latter containing 20.9% $CO_2$ and the balance $N_2$ (accurate to ±0.03%). This enables titration of the calibration gas and its subsequent mixing with room air during the inspiratory phase of pumping. In particular, the simulator evenly mixes tank 20.9% $CO_2$ with room air containing 20.9% $O_2$, resulting in a constant respiratory exchange ratio of R=1. The choice of R=1 in the simulator design can be important, as it corresponds to equality of inspired and expired tidal volumes, thus obviating potential errors in computing $\dot{V}_{O2}$ resulting from measurement of expiratory flow only. The exact $\dot{V}_{O2}$ and $\dot{V}_{CO2}$ values can vary slightly depending on RH, temperature, and calibration gas $CO_2$ content. The calibration gas flow controls are calibrated under ambient temperature and pressure dry (ATPD) conditions, so to derive the standard temperature and pressure dry (STPD) values, the actual barometric pressure, room temperature, and RH can be measured by the M3 system.

The separation of metabolic rates from the level of ventilation can be helpful to assessing $\dot{V}O_2$ and $\dot{V}_{CO2}$ over a wide range (e.g., $\dot{V}_{O2}$ and $\dot{V}_{CO2}$ values from 0 to 4 L/min). The mass flow rate of the calibration gas ranges from 0-20 L/minute and the calibration gas is ~20.9% $CO_2$; also, $\dot{V}_{CO2}=\dot{V}_{O2}$. As a result, any chosen $\dot{V}_{O2}=\dot{V}_{CO2}$ value in the 0 to 4 L/min range can be delivered over a spectrum of $\dot{V}_E$ values; the simulated $\dot{V}_{O2}$ and $\dot{V}_{CO2}$ values will always be equal no matter how $\dot{V}_E$ is adjusted. This is because $\dot{V}_{O2}=\dot{V}_E \times F_{E,O2}=\dot{V}_{CO2}=\dot{V}_E \times F_{E,CO2}$. If $\dot{V}_E$ changes, there will be corresponding offsetting changes in $F_{E,O2}$ and $F_{E,CO2}$, such that $\dot{V}_{O2}=\dot{V}_{CO2}$=constant (i.e., lower $\dot{V}_E$ values will result in higher gas concentrations, and vice versa). The value of the constant is determined solely by the selected mass flow rate of the calibration gas. Similarly, any error in the simulated value of $\dot{V}_E$ will not affect the values of $\dot{V}_{O2}$ and $\dot{V}_{CO2}$, since $F_{E,O2}$ and $F_{E,CO2}$ will change to offset the error in $\dot{V}_E$. The Vacumed $\dot{V}_{O2}$ and $\dot{V}_{CO2}$ values are accurate to ±1%.

Theory of Operation

Without intending to be bound by any particular theory of operation, possible theories of operation are explored below.

The differential equation describing the mixing of the monitored subject's expired $O_2$ with gas in the tank (e.g., initially room air) is:

$$\dot{F}_{T,O2}(t)=\dot{V}_E(t)[F_{E,O2}(t)-F_{T,O2}(t)]/V_T \quad (1)$$

where $\dot{F}_{T,O2}(t)$ is the rate of change of the volumetric fraction of $O_2$ in the tank at time t, $F_{E,O2}(t)$ is the volumetric fraction of $O_2$ in exhaled gas entering the tank at time t, $\dot{V}_E(t)$ is the volume flow of exhaled gas entering the tank at time t, and $V_T$ is the tank volume. Equation 1 states that the rate of change of the $O_2$ fraction in the tank at time t, $\dot{F}_{T,O2}(t)$, must equal the rate at which the $O_2$ fraction enters the tank, $\dot{V}_E(t) \times F_{E,O2}(t)/V_T$, minus the rate at which the $O_2$ fraction exits the tank, $\dot{V}_E(t) F_{T,O2}(t)/V_T$. Equation 1 may be rewritten as:

$$V_T\dot{F}_{T,O2}(t)+\dot{V}_E(t)F_{T,O2}(t)=\dot{V}_E(t)F_{E,O2}(t), \quad (2)$$

where the term $\dot{V}_E(t) F_{E,O2}(t)$ represents the volumetric flow of $O_2$ in the exhaled gas. In the present context, it will be assumed that the user does not initiate measurement until a steady state in activity level has been achieved, in which case Equation 2 may be further simplified. In particular, since only the volume of $O_2$ consumed over a measured period of time (to be defined below) is of current interest, not the breath-to-breath variations, it can be acceptable to redefine both $\dot{V}_E(t)$ and $F_{E,O2}(t)$ as non-time-varying quantities, having values that are, in effect, averaged over the measurement period. As such, Equation 2 may be rewritten as:

$$V_T\dot{F}_{T,O2}(t)+\dot{V}_E F_{T,O2}(t)=\dot{V}_E F_{E,O2}. \quad (3)$$

The solution to this linear first-order differential equation with constant coefficients is:

$$F_{T,O2}(t)=F_{E,O2}+(F_{I,O2}-F_{E,O2})e^{-t(VE/VT)}, \quad (4)$$

where $F_{I,O2}$ is the volumetric fraction of $O_2$ in room air. The solution for $F_{T,O2}(t)$ in Equation 4 is a decreasing exponential function with initial value $F_{I,O2}$=0.2093, final value $F_{E,O2}$, and time constant $\tau=V_T/\dot{V}_E$. Using the same approach, the volumetric fraction of $CO_2$ in the tank at time t can be written as:

$$F_{T,CO2}(t)=F_{E,CO2}+(F_{I,CO2}-F_{E,CO2})e^{-t(VE/VT)}, \quad (5)$$

where $F_{I,CO2}$ is the volumetric fraction of $CO_2$ in room air. The solution for $F_{T,CO2}(t)$ represented by Equation 5 is an increasing exponential function with initial value $F_{I,CO2}$=0.0004, final value $F_{E,CO2}$, and $\tau=V_T/\dot{V}_E$. It is well known that the equation for oxygen consumption may be written as:

$$\dot{V}_{O2}=(\dot{V}_I \times F_{I,O2})-(\dot{V}_E \times F_{E,O2}) \quad (6)$$

The requirement to measure $\dot{V}_I$ may be obviated through a substitution based on the Haldane transformation:

$$\dot{V}_I \times F_{I,N2}=\dot{V}_E \times F_{E,N2}, \quad (7)$$

where $F_{I,N2}$=0.7903 is the volumetric fraction of $N_2$ in room air and $F_{E,N2}$ is the volumetric fraction of $N_2$ in exhalations. Based on the fact that nitrogen is neither produced nor consumed by the body, the Haldane transformation states that under steady-state conditions, the inspired and expired volumes of nitrogen are equal. Rearranging Eq. 7 to isolate $\dot{V}_I$, and then substituting for $\dot{V}_I$ in Eq. 6 yields:

$$\dot{V}_{O2}=\dot{V}_E[(F_{E,N2}/F_{I,N2})\times F_{I,O2}-F_{E,O2}] \quad (8)$$

Transforming Equation 8 from body temperature and pressure saturated (BTPS) conditions to standard temperature and pressure dry (STPD) conditions using the ideal gas law, and since $F_{E,N2}=1-F_{E,O2}-F_{E,CO2}$, Equation 8 may be rewritten as:

$$\dot{V}_{O2}=A \times \dot{V}_E[(F_{I,O2}/F_{I,N2})\times(1-F_{E,O2}-F_{E,CO2})-F_{E,O2}], \quad (9)$$

where the scale factor $A$ is:

$$A=[273.15/(273.15+T_T)]\times[(P_T-P_{T,H2O})/101.3],$$

$T_T$ is the gas tank temperature (in degrees C.; the term 273.15 converts it into degrees K), $P_T$ is the tank barometric pressure (in kPa; the divisor 101.3 is the standard pressure in kPa), which is the same as the ambient atmospheric pressure, and $P_{T,H2O}$ is the tank water vapor pressure at temperature $T_T$.

Since the conduit can reduce water vapor content so that the tank water vapor pressure to equal that of ambient air, $P_{T,H2O}=RH \times P_{SVP}$, where $P_{SVP}$, the saturation vapor pressure, is a function of the tank temperature, $T_T$; $P_{SVP}$ is readily computed using the Goff-Gratch equation. For example, at 21 degrees C., $P_{SVP}$=2.5 kPa.

Values for $F_{E,O2}$ and $F_{E,CO2}$ for use in solving Equation 9 can be obtained using Equations 4 and 5, respectively, by fitting these equations to the measured values of $F_{T,O2}(t)$ and $F_{T,CO2}(t)$. The steady-state (i.e., $t \to \infty$) values of $F_{T,O2}(t)$ and $F_{T,CO2}(t)$ yield $F_{E,O2}$ and $F_{E,CO2}$, respectively. The time constant, $\tau=V_T/\dot{V}_E$, is the same for Equations 4 and 5; the value of VT will be known in advance (i.e., precisely measured a priori via the ideal gas law). Although there can be small oscillations in the measured $F_{T,O2}(t)$ and $F_{T,CO2}(t)$ responses that occur during breathing, these need not impact the results, as the exponential responses in Equations 4 and 5 can be modeled using the "best-fit" to the response data to establish the time constant $\tau$. Knowing $\tau$ and $V_T$, $\dot{V}_E=V_T/\tau$.

To compute the respiratory exchange ratio, $R=\dot{V}_{CO2}/\dot{V}_{O2}$, the production of $CO_2$ can first be calculated using an equation that is similar to that for the consumption of $O_2$:

$$\dot{V}_{CO2}=(F_{E,CO2} \times \dot{V}_E)-(F_{I,CO2} \times \dot{V}_I). \quad (10)$$

Substituting $\dot{V}_I$ from Equation 7 into Equation 10, performing algebra as above, and adjusting to STPD conditions yields:

$$\dot{V}_{CO2}=A \times \dot{V}_E[(F_{E,CO2})-(F_{I,CO2})\times(1-F_{E,O2}-F_{E,CO2})/(F_{I,N2})] \quad (11)$$

As for Equation 9, all quantities needed to compute $\dot{V}_{CO2}$ in Equation 11 are available; therefore R can also be computed. With the proposed approach, there need be no dependence of the solution on the sensor time constants, since both exponential curves defined by Equations 4 and 5 can be aligned (e.g., shifted left to account for measurement delay) based on the first deviations from the initial conditions (viz., $F_{T,O2}(0)=0.2093$ and $F_{T,CO2}(0)=0.0004$).

Measurement trials during a user's metabolic steady state (rest or exercise) can be run for the time period necessary until, for example, deviations in $F_{T,O2}$ fall below a threshold value, such as $\varepsilon_{FT,O2}=0.01$ (i.e., 1%), achievement of a near steady state in tank volumetric $CO_2$ fraction (i.e., $F_{T,CO2}$ deviations falling below a threshold amount, $\varepsilon_{FT,CO2}$), and/or or a fixed time period elapses. The exponential curves of Equations 4 and 5 can then be fitted and the steady-state (i.e., $t \to \infty$) values for $F_{T,O2}$ and $F_{T,CO2}$ established. The values for $\tau=V_T/\dot{V}_E$, estimated separately based on Equations 4 and 5, can be averaged to establish the final value for $\dot{V}_E$ for use in computing $\dot{V}_{O2}$ (Eq. 9) and $\dot{V}_{CO2}$ (Eq. 11). The simplicity of the proposed M3 system can be especially advantageous in clinical applications (e.g., enteral or parenteral nutrition, cardiac catheterization laboratory, etc.), field applications (e.g., biological anthropology), and epidemiological surveys, where a minimum of required ancillary equipment and associated technical expertise can represent a significant advantage. In addition to research, health, fitness, altitude studies, and/or weight loss applications of IC, clinical applications can include: nutritional management of acutely ill and critically ill patients (even those on mechanical ventilators) receiving enteral or parenteral nutrition (which requires measurement of RMR and R); cardiac catheterization laboratory based assessment of the severity of heart failure, pulmonary arterial hypertension, and/or valvular heart disease; assessing the relationship between $O_2$ delivery ($\dot{D}_{O2}$) and uptake ($\dot{V}_{O2}$) in managing acutely ill patients having impaired cardiorespiratory function; and/or monitoring patients during weaning from mechanical ventilators, determining respiratory response to increased $CO_2$ concentrations, and similar assessments.

Figure 6:
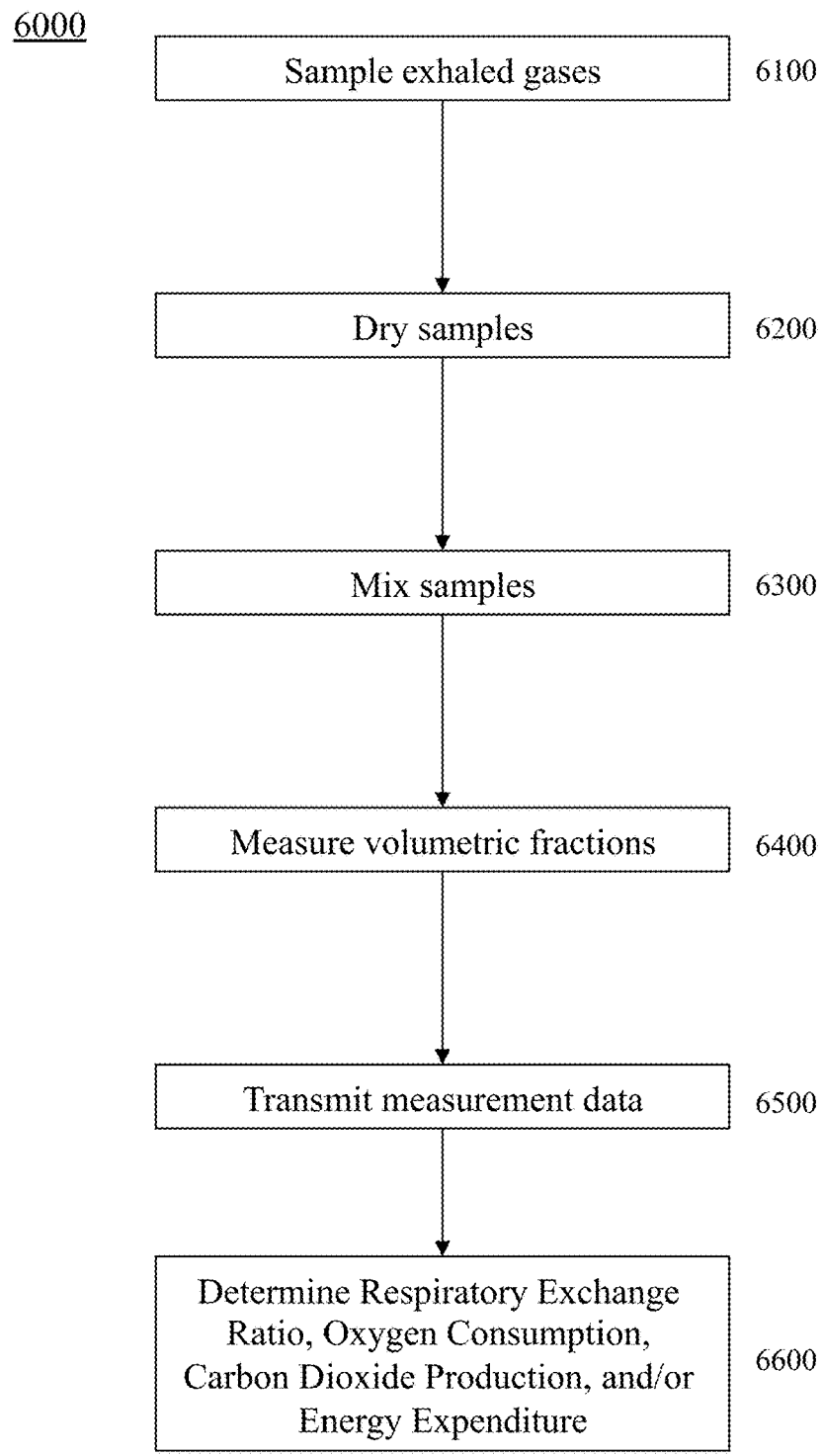
FIG. 6 is a flowchart of an exemplary embodiment of a method.

FIG. 6 is a flowchart of an exemplary embodiment of a method 6000. At activity 6100, exhaled gases are sampled. At activity 6200, the samples are dried and/or conveyed from the flow tube toward a mixing tank. At activity 6300, the samples are mixed. At activity 6400, volumetric fractions of $O_2$ and $CO_2$ are measured within the tank. At activity 6500, the measurement data are transmitted from the tank to an external information device. At activity 6600, respiratory exchange ratio (R), $\dot{V}_{O2}$, $\dot{V}_{CO2}$, and/or an energy expenditure (EE) are determined.

Figure 7:
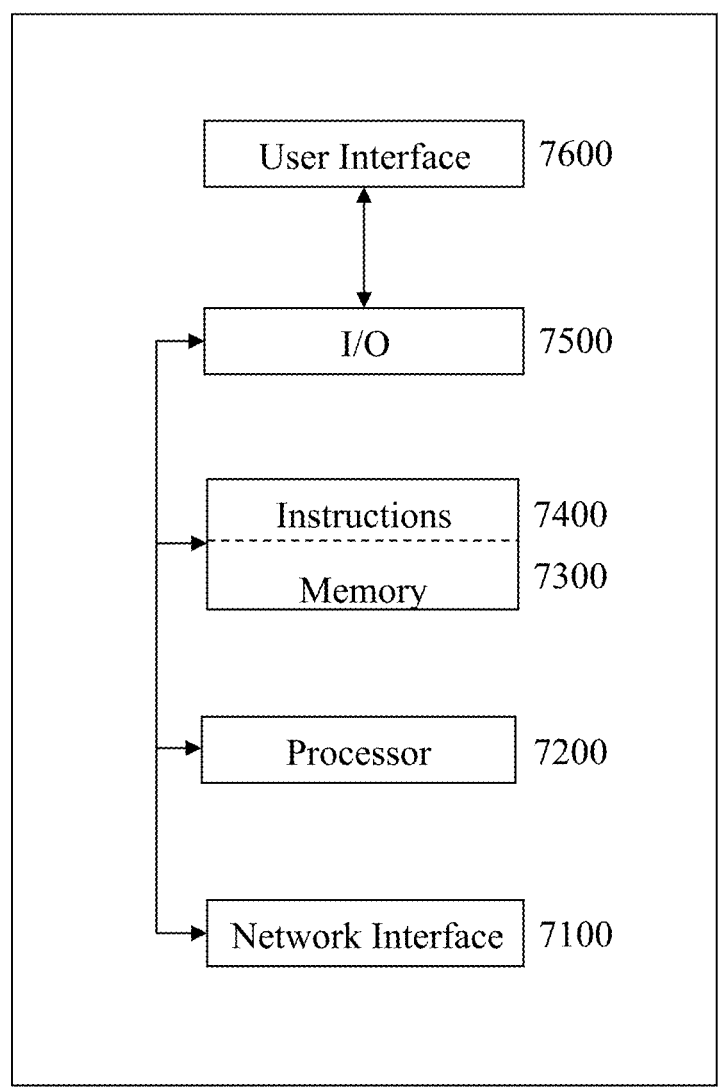
FIG. 7 is a block diagram of an exemplary embodiment of an information device.

FIG. 7 is a block diagram of an exemplary embodiment of an information device 7000, which in certain operative embodiments can comprise, for example, tank information device 108 and/or external information device 121 or 122 of FIG. 1. Information device 7000 can comprise any of numerous transform circuits, which can be formed via any of numerous communicatively-, electrically-, magnetically-, optically-, fluidically-, and/or mechanically-coupled physical components, such as for example, one or more network interfaces 7100, one or more processors 7200, one or more memories 7300 containing instructions 7400, one or more input/output (I/O) devices 7500, and/or one or more user interfaces 7600 coupled to I/O device 7500, etc.

In certain exemplary embodiments, via one or more user interfaces 7600, such as a graphical user interface, a user can view a rendering of information related to researching, designing, modeling, analyzing, evaluating, testing, creating, developing, building, manufacturing, operating, maintaining, storing, marketing, selling, delivering, selecting, specifying, requesting, ordering, receiving, returning, rating, and/or recommending any of the products, services, methods, user interfaces, and/or information described herein.

Certain exemplary embodiments can provide a flowmeter-free indirect calorimetry system configured to facilitate determination of the oxygen consumption, carbon dioxide production, respiratory exchange ratio, and/or energy expenditure of a mammal, the system comprising:
  a mixing tank configured to contain a mixture comprising at least a portion of each of a group of samples of exhaled gases provided by the mammal during a predetermined time period;
  a flow tube configured to route each of the group of samples toward the mixing tank;
  a conduit configured to convey the exhaled gases from the flow tube toward the mixing tank and configured to reduce a water vapor pressure of the exhaled gases within the flow tube to approximately a water vapor pressure in air outside the flow tube;
  a plurality of sensors comprising:
    an oxygen sensor configured to measure a volumetric oxygen fraction of the mixture in the mixing tank;
    a self-calibrating carbon dioxide sensor configured to measure a volumetric carbon dioxide fraction of the mixture in the mixing tank;
    a relative humidity sensor configured to measure a relative humidity of the mixture in the mixing tank;
    a temperature sensor configured to measure a temperature of the mixture in the mixing tank; and/or
    a barometric pressure sensor configured to measure a barometric pressure of the mixture in the mixing tank;
  a one-way inlet valve configured to prevent the mixture from escaping from the tank via the conduit;
  a vacuum pump configured to induce flow of the exhaled gases to the tank via the flow tube;
  a wireless transceiver configured to convey sensor measurement data; and/or
  a battery back configured to power the sensors and/or the wireless transceiver;
  wherein:
    the tank is formed from a non-conductive plastic;
    the tank comprises a removable lid and a gasket configured to form a gas-tight seal between the tank and the lid;
    the tank is configured to promote homogeneous mixing of the samples;
    the tank comprises an inlet port and an outlet port, an entrance to the inlet port aligned perpendicularly to an entrance to the outlet port;
    the battery back is located on a bottom of the tank;
    the barometric pressure sensor is integrated with the oxygen sensor;
    the temperature sensor is integrated with the carbon dioxide sensor;
    the oxygen consumption, carbon dioxide production, respiratory exchange ratio, and/or energy expenditure can be determined without directly measuring the breath-by-breath volumetric gas fractions of exhalations by the mammal;
    there be no gas sensors in the conduit; and/or
    the relative humidity sensor is integrated with the carbon dioxide sensor.

A flowmeter-free indirect calorimetry method that is configured to facilitate determination of the oxygen consumption, carbon dioxide production, respiratory exchange ratio, and/or energy expenditure of a mammal the method comprising activities comprising:

sampling at least a portion of each of a group of samples of exhaled gases provided by the mammal during a predetermined time period, the flow tube configured to direct each of the group of samples toward a mixing tank;

conveying the samples through a conduit toward the mixing tank, the conduit configured to reduce a water vapor pressure of the exhaled gases within the flow tube to approximately a water vapor pressure in air outside the flow tube;

in the mixing tank, mix the samples to form a mixture;

via an oxygen sensor, measuring a volumetric oxygen fraction of the mixture in the mixing tank;

via a self-calibrating carbon dioxide sensor, measuring a volumetric carbon dioxide fraction of the mixture in the mixing tank;

measuring a relative humidity of the mixture in the mixing tank;

measuring a temperature of the mixture in the mixing tank;

measuring a barometric pressure of the mixture in the mixing tank;

prior to the mixing tank containing the mixture, and via the oxygen sensor, measuring a volumetric oxygen fraction of a gaseous content of the tank;

prior to the mixing tank containing the mixture, and via the carbon dioxide sensor, measuring a volumetric carbon dioxide fraction of the gaseous content of the tank;

inducing flow of the samples to the tank via a vacuum pump;

wirelessly transmitting sensor measurement data for determination of the oxygen consumption, carbon dioxide production, respiratory exchange ratio, and/or energy expenditure based on the volumetric oxygen fraction and the volumetric carbon dioxide fraction;

wirelessly transmitting the volumetric oxygen fraction;

wirelessly transmitting the volumetric carbon dioxide fraction;

wirelessly transmitting the relative humidity;

wirelessly transmitting the temperature;

wirelessly transmitting the barometric pressure; and/or determining the the oxygen consumption, carbon dioxide production, respiratory exchange ratio, and/or energy expenditure based on the volumetric oxygen fraction and the volumetric carbon dioxide fraction;

wherein:
the determined oxygen consumption, carbon dioxide production, respiratory exchange ratio, and/or energy expenditure is substantially independent of a time constant of the oxygen sensor and a time constant of the carbon dioxide sensor;

the oxygen consumption, carbon dioxide production, respiratory exchange ratio, and/or energy expenditure can be determined without directly measuring the breath-by-breath volumetric gas fractions of exhalations by the mammal;

there be no gas sensors in the conduit; and/or a pressure in the tank remains at substantially atmospheric pressure throughout said measuring activities.

Definitions

When the following phrases are used substantively herein, the accompanying definitions apply. These phrases and definitions are presented without prejudice, and, consistent with the application, the right to redefine these phrases via amendment during the prosecution of this application or any application claiming priority hereto is reserved. For the purpose of interpreting a claim of any patent that claims priority hereto, each definition in that patent functions as a clear and unambiguous disavowal of the subject matter outside of that definition.

a—at least one.

about—around and/or approximately.

above—at a higher level.

across—from one side to another.

activity—an action, act, deed, function, step, and/or process and/or a portion thereof adapt—to design, make, set up, arrange, shape, configure, and/or make suitable and/or fit for a specific purpose, function, use, and/or situation.

adapter—a device used to effect operative compatibility between different parts of one or more pieces of an apparatus or system.

after—following in time and/or subsequent to.

air—the earth's atmospheric gas.

align—To arrange in a line or so as to be substantially parallel.

along—through, on, beside, over, in line with, and/or parallel to the length and/or direction of; and/or from one end to the other of.

and—in conjuction with.

and/or—either in conjunction with or in alternative to.

any—one, some, every, and/or all without specification.

apparatus—an appliance or device for a particular purpose.

approximately—about and/or nearly the same as.

around—about, surrounding, and/or on substantially all sides of; and/or approximately.

as long as—if and/or since.

associate—to join, connect together, and/or relate.

at—in, on, and/or near.

at least—not less than, and possibly more than.

atmospheric pressure—the pressure exerted by the earth's atmosphere at any given point, being the product of the mass of the atmospheric column of the unit area above the given point and of the gravitational acceleration at the given point; typically approximately 14.7 psia.

automatic—performed via an information device in a manner essentially independent of influence and/or control by a user. For example, an automatic light switch can turn on upon "seeing" a person in its "view", without the person manually operating the light switch.

barometric pressure—the pressure exerted by the earth's atmosphere at any given point.

based—being derived from, conditional upon, and/or dependent upon.

battery—a unit source of direct current (DC) voltage that comprises a plurality of voltaic cells electrically connected in series and/or parallel to increase available voltage or power from a single cell.

between—in a separating interval and/or intermediate to.

Boolean logic—a complete system for logical operations.

bottom—a lowest part of an object relative to a point of reference, the object in a predetermined orientation relative to the point of reference.

by—via and/or with the use and/or help of calibrate—to check, adjust, and/or determine by comparison with a standard (the graduations of a quantitative measuring instrument).

can—is capable of, in at least some embodiments.

carbon dioxide—a colourless odourless incombustible gas present in the atmosphere, having a formula $CO_2$, and formed during respiration, the decomposition and combustion of organic compounds, and in the reaction of acids with carbonates: used in carbonated drinks, fire extinguishers, and as dry ice for refrigeration.

cause—to bring about, provoke, precipitate, produce, elicit, be the reason for, result in, and/or effect.

circuit—a physical system comprising, depending on context: an electrically conductive pathway, an information transmission mechanism, and/or a communications connection, the pathway, mechanism, and/or connection established via a switching device (such as a switch, relay, transistor, and/or logic gate, etc.); and/or an electrically conductive pathway, an information transmission mechanism, and/or a communications connection, the pathway, mechanism, and/or connection established across two or more switching devices comprised by a network and between corresponding end systems connected to, but not comprised by the network.

composition of matter—a combination, reaction product, compound, mixture, formulation, material, and/or composite formed by a human and/or automation from two or more substances and/or elements.

comprising—including but not limited to.

concentration—a measure of how much of a given substance is mixed, dissolved, contained, and/or otherwise present in and/or with another substance, and/or a measure of the amount of dissolved substance contained per unit of volume and/or the amount of a specified substance in a unit amount of another substance, both measures defining a structure of a composition that comprises both substances.

conduit—a tube, channel, and/or duct for substantially enclosing electric wires, cables, and/or fluids.

configure—to design, arrange, set up, shape, and/or make suitable and/or fit for a specific purpose, function, use, and/or situation.

connect—to join or fasten together.

containing—including but not limited to.

content—that which is contained.

convert—to transform, adapt, and/or change.

convey—to transmit, transport, guide, and/or carry.

corresponding—related, associated, accompanying, similar in purpose and/or position, conforming in every respect, and/or equivalent and/or agreeing in amount, quantity, magnitude, quality, and/or degree.

coupleable—capable of being joined, connected, and/or linked together.

coupling—linking in some fashion.

create—to bring into being.

data—distinct pieces of information, usually formatted in a special or predetermined way and/or organized to express concepts, and/or represented in a form suitable for processing by an information device.

data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.

define—to establish the meaning, relationship, outline, form, and/or structure of; and/or to precisely and/or distinctly describe and/or specify.

derive—to receive, obtain, and/or produce from a source and/or origin.

determination—an act of calculating, computing, making, and/or arriving at a decision.

determine—to find out, obtain, calculate, decide, deduce, ascertain, and/or come to a decision, typically by investigation, reasoning, and/or calculation.

determining—to find out or come to a decision about by investigation, reasoning, or calculation.

device—a machine, manufacture, and/or collection thereof.

digital—non-analog and/or discrete.

direct—to point, aim, and/or send toward a place or object, and/or to cause to move in or follow a predetermined course.

during—at some time in a time interval.

each—every one of a group considered individually.

EE—Energy Expenditure effective—sufficient to bring about, provoke, elicit, and/or cause.

embodiment—an implementation, manifestation, and/or concrete representation.

entrance—a location and/or direction by which to enter.

escape—to get free and/or to break loose from confinement.

estimate—(n) a calculated value approximating an actual value; (v) to calculate and/or determine approximately and/or tentatively.

exemplary—serving as an example, instance, and/or illustration.

exhale—to breathe out and/or to expel (breath, tobacco smoke, etc.) from the lungs.

facilitate—to help bring about, encourage, and/or allow.

first—an initial element in a set.

flow—(n) a stream and/or current; (v) to move and/or run smoothly with unbroken continuity, as in the manner characteristic of a fluid.

flowmeter—a device configured to measure a flowrate of a fluid.

flow tube—a device to extract a small portion of a fluid flow in order to perform measurements for—with a purpose of formed—constructed.

fractional—constituting or comprising a part or fraction of a possible whole or entirety.

free—lacking and/or not having.

from—used to indicate a source, origin, and/or location thereof.

further—in addition.

gas—a substance in a gaseous state, that is, in a state of matter distinguished from the solid and liquid states by relatively low density and viscosity, relatively great expansion and contraction with changes in pressure and temperature, the ability to diffuse readily, and the spontaneous tendency to become distributed uniformly throughout any container; and/or a substance in a gaseous state.

gas-tight—not susceptible to substantial leakage.

gaseous—existing in the state of a gas and/or pertaining to and/or having the characteristics of gas; and/or not solid or liquid.

gasket—any of a wide variety of seals or packings used between matched parts and/or joints to prevent the escape of a fluid.

generate—to create, produce, give rise to, and/or bring into existence.

group—(n.) a number of individuals or things considered together because of similarities; (v.) to associate a number of individuals or things such that they are considered together and/or caused to have similar properties.

group—a plurality of determined units.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

having—including but not limited to.

homogeneous—uniform in structure or composition.

human-machine interface—hardware and/or software adapted to render information to a user and/or receive information from the user; and/or a user interface.

including—including but not limited to.

independent—without dependence upon and/or regard for another.

indirect calorimetry—a method by which energy metabolism is estimated in vivo starting from gas exchange measurements (carbon dioxide production and oxygen consumption during rest and steady-state exercise).

induce—to bring about and/or cause to occur.

information device—any device capable of processing data and/or information, such as any general purpose and/or special purpose computer, such as a personal computer, workstation, server, minicomputer, mainframe, supercomputer, computer terminal, laptop, tablet computer (such as an iPad-like device), wearable computer, Personal Digital Assistant (PDA), mobile terminal, Bluetooth device, communicator, "smart" phone (such as an iPhone-like device), messaging service (e.g., Blackberry) receiver, pager, facsimile, cellular telephone, traditional telephone, telephonic device, embedded controller, programmed microprocessor or microcontroller and/or peripheral integrated circuit elements, ASIC or other integrated circuit, hardware electronic logic circuit such as a discrete element circuit, and/or programmable logic device such as a PLD, PLA, FPGA, or PAL, or the like, etc. In general, any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc. In information device can be a component of and/or augment another device, such as an appliance, machine, tool, robot, vehicle, television, printer, "smart" utility meter, etc.

inhalation—The act or an instance of inhaling.

inhale—inspire and/or to draw (air or smoke, for example) into the lungs by breathing.

initialize—to prepare something for use and/or some future event.

inlet—an entrance and/or opening.

input/output (I/O) device—any device adapted to provide input to, and/or receive output from, an information device. Examples can include an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, switch, relay, haptic device, vibrator, tactile simulator, and/or tactile pad, potentially including a port to which an I/O device can be attached or connected.

install—to connect or set in position and prepare for use.

instructions—directions, which can be implemented as hardware, firmware, and/or software, the directions adapted to perform a particular operation and/or function via creation and/or maintenance of a predetermined physical circuit.

integrated—formed or united into a whole or into another entity.

into—to a condition, state, or form of is—to exist in actuality.

lid—a removable or hinged cover for a hollow container, receptacle, and/or box.

located—situated approximately in a particular spot and/or position.

logic gate—a physical device adapted to perform a logical operation on one or more logic inputs and to produce a single logic output, which is manifested physically. Because the output is also a logic-level value, an output of one logic gate can connect to the input of one or more other logic gates, and via such combinations, complex operations can be performed. The logic normally performed is Boolean logic and is most commonly found in digital circuits. The most common implementations of logic gates are based on electronics using resistors, transistors, and/or diodes, and such implementations often appear in large arrays in the form of integrated circuits (a.k.a., IC's, microcircuits, microchips, silicon chips, and/or chips). It is possible, however, to create logic gates that operate based on vacuum tubes, electromagnetics (e.g., relays), mechanics (e.g., gears), fluidics, optics, chemical reactions, and/or DNA, including on a molecular scale. Each electronically-implemented logic gate typically has two inputs and one output, each having a logic level or state typically physically represented by a voltage. At any given moment, every terminal is in one of the two binary logic states ("false" (a.k.a., "low" or "0") or "true" (a.k.a., "high" or "1"), represented by different voltage levels, yet the logic state of a terminal can, and generally does, change often, as the circuit processes data. Thus, each electronic logic gate typically requires power so that it can source and/or sink currents to achieve the correct output voltage. Typically, machine-implementable instructions are ultimately encoded into binary values of "0"s and/or "1"s and, are typically written into and/or onto a memory device, such as a "register", which records the binary value as a change in a physical property of the memory device, such as a change in voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc. An exemplary register might store a value of "01101100", which encodes a total of 8 "bits" (one byte), where each value of either "0" or "1" is called a "bit" (and 8 bits are collectively called a "byte"). Note that because a binary bit can only have one of two different values (either "0" or "1"), any physical medium capable of switching between two saturated states can be used to represent a bit. Therefore, any physical system capable of representing binary bits is able to represent numerical quantities, and potentially can manipulate those numbers via particular encoded machine-implementable instructions. This is one of the basic concepts underlying digital computing. At the register and/or gate level, a computer does not treat these "0"s and "1"s as numbers per se, but typically as voltage levels (in the case of an electronically-implemented computer), for example, a high voltage of approximately +3 volts might represent a "1" or "logical true" and a low voltage of approximately 0 volts might represent a "0" or "logical false" (or vice versa, depending on how the circuitry is designed). These high and low voltages (or other physical properties, depending on the nature of the implementation) are typically fed into a series of logic gates, which in turn, through the correct logic design, produce the physical and logical results specified by the particular encoded machine-implementable instructions. For example, if the encoding request a calculation, the logic gates might add the first two bits of the encoding together, produce a result "1" ("0"+"1"="1"), and then write this result into another register for subsequent retrieval and reading. Or, if the encoding is a request for some kind of service, the logic gates might in turn access or write into some other registers which would in turn trigger other logic gates to initiate the requested service.

logical—a conceptual representation.

machine-implementable instructions—directions adapted to cause a machine, such as an information device, to perform one or more particular activities, operations, and/or functions via forming a particular physical circuit. The directions, which can sometimes form an entity called a "processor", "kernel", "operating system", "program", "application", "utility", "subroutine", "script", "macro", "file", "project", "module", "library", "class", and/or "object", etc., can be embodied and/or encoded as machine code, source code, object code, compiled code, assembled code, interpretable code, and/or executable code, etc., in hardware, firmware, and/or software.

machine-readable medium—a transitory and/or non-transitory physical and/or tangible structure via which a machine, such as an information device, computer, microprocessor, and/or controller, etc., can store or carry one or more machine-implementable instructions, data structures, data, and/or information and/or obtain one or more stored machine-implementable instructions, data structures, data, and/or information. Examples include a memory device, punch card, player-piano scroll, etc.

mammal—any of various warm-blooded vertebrate animals of the class Mammalia, including humans, characterized by a covering of hair on the skin and, in the female, milk-producing mammary glands for nourishing the young.

may—is allowed and/or permitted to, in at least some embodiments.

measure—(n) a quantity ascertained by comparison with a standard and/or manual and/or automatic observation. (v) to physically sense, and/or determine a value and/or quantity of something relative to a standard.

measurement—a value of a variable, the value determined by manual and/or automatic observation.

medium—any substance or material, such as one or more solids, liquids, vapors, fluids, water, and/or air, etc.

memory device—an apparatus capable of storing, sometimes permanently, machine-implementable instructions, data, and/or information, in analog and/or digital format. Examples include at least one non-volatile memory, volatile memory, register, relay, switch, Random Access Memory, RAM, Read Only Memory, Erasable Programmable Read-Only Memory (EPROM), Electrically Erasable Programmable Read-Only Memory (EEPROM), ROM, flash memory, magnetic media, hard disk, floppy disk, magnetic tape, optical media, optical disk, compact disk, CD, digital versatile disk, DVD, and/or raid array, etc. The memory device can be coupled to a processor and/or can store and provide instructions adapted to be executed by processor, such as according to an embodiment disclosed herein.

method—one or more acts that are performed upon subject matter to be transformed to a different state or thing and/or are tied to a particular apparatus, said one or more acts not a fundamental principal and not preempting all uses of a fundamental principal.

mix—to combine and/or blend into one mass, stream, and/or mixture.

mixture—a composition of two or more substances that are not chemically combined with each other and are capable of being separated.

molecule—the smallest particle of a substance that retains the chemical and physical properties of the substance and is composed of two or more atoms; and/or a group of like or different atoms held together by chemical forces.

near—a distance of less than approximately [X].

network—a communicatively coupled plurality of nodes, communication devices, and/or information devices. Via a network, such nodes and/or devices can be linked, such as via various wireline and/or wireless media, such as cables, telephone lines, power lines, optical fibers, radio waves, and/or light beams, etc., to share resources (such as printers and/or memory devices), exchange files, and/or allow electronic communications therebetween. A network can be and/or can utilize any of a wide variety of sub-networks and/or protocols, such as a circuit switched, public-switched, packet switched, connection-less, wireless, virtual, radio, data, telephone, twisted pair, POTS, non-POTS, DSL, cellular, telecommunications, video distribution, cable, radio, terrestrial, microwave, broadcast, satellite, broadband, corporate, global, national, regional, wide area, backbone, packet-switched TCP/IP, IEEE 802.03, Ethernet, Fast Ethernet, Token Ring, local area, wide area, IP, public Internet, intranet, private, ATM, Ultra Wide Band (UWB), Wi-Fi, BlueTooth, Airport, IEEE 802.11, IEEE 802.11a, IEEE 802.11b, IEEE 802.11g, X-10, electrical power, 3G, 4G, multi-domain, and/or multi-zone sub-network and/or protocol, one or more Internet service providers, one or more network interfaces, and/or one or more information devices, such as a switch, router, and/or gateway not directly connected to a local area network, etc., and/or any equivalents thereof.

network interface—any physical and/or logical device, system, and/or process capable of coupling an information device to a network. Exemplary network interfaces comprise a telephone, cellular phone, cellular modem, telephone data modem, fax modem, wireless transceiver, communications port, ethernet card, cable modem, digital subscriber line interface, bridge, hub, router, or other similar device, software to manage such a device, and/or software to provide a function of such a device.

no—an absence of and/or lacking any.

non-conductive—not having a substantial ability to transfer electrical current at a given voltage.

one—being and/or amounting to a single unit, individual, and/or entire thing, item, and/or object.

one-way—permitting movement in one direction only.

operable—practicable and/or fit, ready, and/or configured to be put into its intended use and/or service.

or—a conjunction used to indicate alternatives, typically appearing only before the last item in a group of alternative items.

outlet—an exit, vent, and/or passage for escape and/or exit.

outside—beyond a range, boundary, and/or limit; and/or not within.

oxygen—a nonmetallic element, which constitutes approximately 21 percent of the earth's atmosphere by volume, which occurs as a diatomic gas, O2, and which is assigned atomic number 8, and has atomic weight 15.9994.

packet—a generic term for a bundle of data organized in a specific way for transmission, such as within and/or across a network, such as a digital packet-switching network, and comprising the data to be transmitted and certain control information, such as a destination address.

per—for each and/or by means of.

perceptible—capable of being perceived by the human senses.

period—a time interval.

perpendicular—substantially at a right angle with respect to an axis.

physical—tangible, real, and/or actual.

physically—existing, happening, occurring, acting, and/or operating in a manner that is tangible, real, and/or actual.

plastic—any of a group of synthetic or natural organic materials that may be shaped when soft and then hardened, including many types of resins, resinoids, polymers, cellulose derivatives, casein materials, and proteins: used in place of other materials, as glass, wood, and metals, in construction and decoration, for making many articles, as coatings, and, drawn into filaments, for weaving.

plurality—the state of being plural and/or more than one.

portion—a part, component, section, percentage, ratio, and/or quantity that is less than a larger whole.

power—(n) energy, a measure of energy and/or work, and/or a rate at which work is done, expressed as the amount of work per unit time and commonly measured in units such as watt and horsepower; (v) to energize, such as via applying electricity.

pre-—a prefix that precedes an activity that has occurred beforehand and/or in advance.

predetermine—to determine, decide, and/or establish in advance.

pressure—a measure of force applied uniformly over a surface.

prevent—to hinder, avert, and/or keep from occurring.

prior—before and/or preceding in time or order.

probability—a quantitative representation of a likelihood of an occurrence.

processor—a machine that utilizes hardware, firmware, and/or software and is physically adaptable to perform, via Boolean logic operating on a plurality of logic gates that form particular physical circuits, a specific task defined by a set of machine-implementable instructions. A processor can utilize mechanical, pneumatic, hydraulic, electrical, magnetic, optical, informational, chemical, and/or biological principles, mechanisms, adaptations, signals, inputs, and/or outputs to perform the task(s). In certain embodiments, a processor can act upon information by manipulating, analyzing, modifying, and/or converting it, transmitting the information for use by machine-implementable instructions and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium family of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein. A processor can reside on and use the capabilities of a controller.

product—something produced by human and/or mechanical effort.

project—to calculate, estimate, or predict.

promote—designate as a member of a predetermined group.

provide—to furnish, supply, give, and/or make available.

pump—a machine configured to raise, compress, and/or transfer a fluid.

range—a measure of an extent of a set of values and/or an amount and/or extent of variation.

ratio—a relationship between two quantities expressed as a quotient of one divided by the other.

receive—to get as a signal, take, acquire, and/or obtain.

recommend—to suggest, praise, commend, and/or endorse.

reduce—to make and/or become lesser and/or smaller.

relative humidity—The ratio of the amount of water vapor in the air at a specific temperature to the maximum amount that the air could hold at that temperature, expressed as a percentage.

remain—To continue in the same place, state, and/or condition.

removable—capable of being moved from a place or position occupied.

remove—to eliminate, remove, and/or delete, and/or to move from a place or position occupied.

render—to, e.g., physically, chemically, biologically, electronically, electrically, magnetically, optically, acoustically, fluidically, and/or mechanically, etc., transform information into a form perceptible to a human as, for example, data, commands, text, graphics, audio, video, animation, and/or hyperlinks, etc., such as via a visual, audio, and/or haptic, etc., means and/or depiction, such as via a display, monitor, electric paper, ocular implant, cochlear implant, speaker, vibrator, shaker, force-feedback device, stylus, joystick, steering wheel, glove, blower, heater, cooler, pin array, tactile touchscreen, etc.

repeat—to do again and/or perform again.

repeatedly—again and again; repetitively.

request—to express a desire for and/or ask for.

respiration—the process in living organisms of taking in oxygen from the surroundings and giving out carbon dioxide.

respiratory—relating to, used in, or affecting respiration.

respiratory exchange ratio—a ratio between the amount of carbon dioxide ($CO_2$) produced in metabolism and oxygen ($O_2$) used.

result—(n.) an outcome and/or consequence of a particular action, operation, and/or course; (v.) to cause an outcome and/or consequence of a particular action, operation, and/or course.

route—to direct on a path.

said—when used in a system or device claim, an article indicating a subsequent claim term that has been previously introduced.

sample—(n) a set of elements drawn from and analyzed to estimate the characteristics of a population; and/or a portion, piece, and/or segment that is representative of a whole. (v) to take and/or obtain one or more measurements at random and/or predetermined times.

sampler/diverter—a device configured to sample.

sampling—the act of taking periodic measurements and/or readings of a continuous phenomena, such as an analog signal or fluid flow.

seal—(v.) to shut close, keep close, make fast, keep secure, and/or prevent leakage; (n.) a device configured to shut close, keep close, make fast, keep secure, and/or prevent leakage.

select—to make a choice or selection from alternatives.

self-—without human assistance.

sensor—a device adapted to automatically sense, perceive, detect, and/or measure a physical property (e.g., pressure, temperature, flow, mass, heat, light, sound, humidity, proximity, position, velocity, vibration, loudness, voltage, current, capacitance, resistance, inductance, and/or electromagnetic radiation, etc.) and convert that physical quantity into a signal. Examples include proximity switches, stain gages, photo sensors, thermocouples, level indicating devices, speed sensors, accelerometers, electrical voltage indicators, electrical current indicators, on/off indicators, and/or flowmeters, etc.

server—an information device and/or a process running thereon, that is adapted to be communicatively coupled to a network and that is adapted to provide at least one service for at least one client, i.e., for at least one other information device communicatively coupled to the network and/or for at least one process running on another information device communicatively coupled to the network. One example is a file server, which has a local drive and services requests from remote clients to read, write, and/or manage files on that drive. Another example is an e-mail server, which provides at least one program that accepts, temporarily stores, relays, and/or delivers e-mail messages. Still another example is a database server, which processes database queries. Yet another example is a device server, which provides networked and/or programmable: access to, and/or monitoring, management, and/or control of, shared physical resources and/or devices, such as information devices, printers, modems, scanners, projectors, displays, lights, cameras, security equipment, proximity readers, card readers, kiosks, POS/retail equipment, phone systems, residential equipment, HVAC equipment, medical equipment, laboratory equipment, industrial equipment, machine tools, pumps, fans, motor drives, scales, programmable logic controllers, sensors, data collectors, actuators, alarms, annunciators, and/or input/output devices, etc.

set—a related plurality.

signal—(v) to communicate; (n) one or more automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc., that can encode information, such as machine-implementable instructions for activities and/or one or more letters, words, characters, symbols, signal flags, visual displays, and/or special sounds, etc., having prearranged meaning. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

special purpose computer—a computer and/or information device comprising a processor device having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

special purpose processor—a processor device, having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

species—a class of individuals and/or objects grouped by virtue of their common attributes and assigned a common name; a division subordinate to a genus.

state—a qualitative and/or quantitative description of condition.

store—to place, hold, and/or retain data, typically in a memory.

stream—a steady current of a fluid.

substantially—to a great extent and/or degree.

support—to bear the weight of, especially from below.

switch—(v) to: form, open, and/or close one or more circuits; form, complete, and/or break an electrical and/or informational path; select a path and/or circuit from a plurality of available paths and/or circuits; and/or establish a connection between disparate transmission path segments in a network (or between networks); (n) a physical device, such as a mechanical, electrical, and/or electronic device, that is adapted to switch.

system—a collection of mechanisms, devices, machines, articles of manufacture, processes, data, and/or instructions, the collection designed to perform one or more specific functions.

tank—a container adapted to hold and/or store a solid and/or fluid.

temperature—measure of the average kinetic energy of the molecules in a sample of matter, expressed in terms of units or degrees designated on a standard scale.

that—used as the subject or object of a relative clause.

through—across, among, between, and/or in one side and out the opposite and/or another side of throughout—in, to, through, or during every part of.

time—a measurement of a point in a nonspatial continuum in which events occur in apparently irreversible succession from the past through the present to the future.

time constant—a parameter characterizing the response of a first-order, linear time-invariant (LTI) system to a step input.

time period—an interval of time.

to—a preposition adapted for use for expressing purpose.

toward—in the direction of.

transceiver—a device configured to transmit and/or receive signals.

transform—to change in measurable: form, appearance, nature, and/or character.

transmit—to provide, furnish, supply, send as a signal, and/or to convey (e.g., force, energy, and/or information) from one place and/or thing to another.

treatment—an act, manner, or method of handling and/or dealing with someone and/or something.

tube—an elongate member, such as a pipe, hollow cylinder, or hollow rodlike member, having a longitudinal axis and defining a longitudinal cross-section resembling any substantially closed shape such as, for example, a circle, a non-circle such as an oval (which generally can include a shape that is substantially in the form of an obround, ellipse, limacon, cardioid, cartesian oval, and/or Cassini oval, etc), and/or a polygon such as a triangle, rectangle, square, parallelogram, rhomboid, pentagon, hexagon, the shape of the letter "D", the shape of the letter "P", etc. thereby providing a conduit throughout its length, and having a wall that may vary along its longitudinal length in transverse dimensions and/or shape. Thus, a right circular cylinder is one form of a tube, an elliptic cylinder is another form of a tube having an elliptical longitudinal cross-section, and a generalized cylinder is yet another form of a tube.

upon—immediately or very soon after; and/or on the occasion of.

use—to put into service.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

vacuum—a pressure that is significantly lower than atmospheric pressure and/or approaching 0 psia.

valve—a device that regulates flow through a pipe and/or through an aperture by opening, closing, and/or obstructing a port and/or passageway.

vapor—a gaseous form of a fluid.

via—by way of and/or utilizing.

volumetric fraction—a volume of a constituent $V_i$ divided by the volume of all constituents of the mixture V prior to mixing.

water—a transparent, odorless, tasteless liquid containing approximately 11.188 percent hydrogen and approximately 88.812 percent oxygen, by weight, characterized by the chemical formula H2O, and, at standard pressure (approximately 14.7 psia), freezing at approximately 32° F. or 0 C and boiling at approximately 212° F. or 100 C.

weight—a force with which a body is attracted to Earth or another celestial body, equal to the product of the object's mass and the acceleration of gravity; and/or a factor and/or value assigned to a number in a computation, such as in determining an average, to make the number's effect on the computation reflect its importance, significance, preference, impact, etc.

when—at a time and/or during the time at which.

wherein—in regard to which; and; and/or in addition to.

wireless—any communication technique that transmits a signal that does not require the use of a wire and/or guide connecting a transmitter and a receiver and/or utilizes electromagnetic waves emitted by an antenna (i.e., via an unguided medium), including such communication techniques as sonar, radio, cellular, cellular radio, digital cellular radio, ELF, LF, MF, HF, VHF, UHF, SHF, EHF, radar, microwave, satellite microwave, laser, infrared, etc., but excluding purely visual signaling, such as semaphore, smoke signals, sign language, etc., the communication technique having a baseband and/or carrier frequency ranging from about 1 Hz to about $2\times10^{14}$ Hz (about 200 teraHertz), including all values therebetween, such as for example, about 40 Hz, 6.010 kHz, 8.7 MHz, 4.518 GHz, 30 GHz, etc. and including all subranges therebetween, such as for example, from about 100 kHz to about 100 MHz, about 30 MHz to about 1 GHz, about 3 kHz to about 300 GHz, etc. Wireless communications can include analog and/or digital data, signals, and/or transmissions. Wireless communication can be via any of a plurality of protocols such as, for example, cellular CDMA, TDMA, GSM, GPRS, UMTS, W-CDMA, CDMA2000, TD-CDMA, 802.11a, 802.11b, 802.11g, 802.15.1, 802.15.4, 802.16, and/or Bluetooth, etc.

wirelessly—in a wireless manner.

with—accompanied by.

with regard to—about, regarding, relative to, and/or in relation to.

with respect to—about, regarding, relative to, and/or in relation to.

within—inside the limits of.

without—lacking and/or not accompanied by.

zone—a region and/or volume having at least one predetermined boundary.

Note

Various substantially and specifically practical and useful exemplary embodiments of the claimed subject matter are described herein, textually and/or graphically, including the best mode, if any, known to the inventor(s), for implementing the claimed subject matter by persons having ordinary skill in the art. Any of numerous possible variations (e.g., modifications, augmentations, embellishments, refinements, and/or enhancements, etc.), details (e.g., species, aspects, nuances, and/or elaborations, etc.), and/or equivalents (e.g., substitutions, replacements, combinations, and/or alternatives, etc.) of one or more embodiments described herein might become apparent upon reading this document to a person having ordinary skill in the art, relying upon his/her expertise and/or knowledge of the entirety of the art and without exercising undue experimentation. The inventor(s) expects any person having ordinary skill in the art, after obtaining authorization from the inventor(s), to implement such variations, details, and/or equivalents as appropriate, and the inventor(s) therefore intends for the claimed subject matter to be practiced other than as specifically described herein. Accordingly, as permitted by law, the claimed subject matter includes and covers all variations, details, and equivalents of that claimed subject matter. Moreover, as permitted by law, every combination of the herein described characteristics, functions, activities, substances, and/or structural elements, and all possible variations, details, and equivalents thereof, is encompassed by the claimed subject matter unless otherwise clearly indicated herein, clearly and specifically disclaimed, or otherwise clearly inoperable or contradicted by context.

The use of any and all examples, or exemplary language (e.g., "such as") provided herein, is intended merely to better illuminate one or more embodiments and does not pose a limitation on the scope of any claimed subject matter unless otherwise stated. No language herein should be construed as indicating any non-claimed subject matter as essential to the practice of the claimed subject matter.

Thus, regardless of the content of any portion (e.g., title, field, background, summary, description, abstract, drawing figure, etc.) of this document, unless clearly specified to the contrary, such as via explicit definition, assertion, or argument, or clearly contradicted by context, with respect to any claim, whether of this document and/or any claim of any document claiming priority hereto, and whether originally presented or otherwise:

any particular described feature (e.g., system, sub-system, assembly, device, component, relationship between components, structural element, property, capability, value, characteristic, function, activity, sequence, material, substance, etc.) of any embodiment can be utilized with any feature of any other embodiment there is no requirement for the inclusion of;

any particular described feature or combination of features;

no described characteristic, function, activity, substance, or structural element is "essential"; and within, among, and between any described embodiments:
 any two or more described substances can be mixed, combined, reacted, separated, and/or segregated;
 any described features can be combined, integrated, segregated, and/or duplicated;
 any described activity can be performed manually, semi-automatically, and/or automatically;
 any described activity can be repeated, any activity can be combined with any other described activity, performed by multiple entities, and/or performed in multiple jurisdictions; and
 any described feature can be specifically deleted, omitted, limited, and/or excluded, the sequence of activities can vary, and/or the interrelationship of structural elements can vary.

The use of the terms "a", "an", "said", "the", and/or similar referents in the context of describing various embodiments (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted.

When any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate sub-range defined by such separate values is incorporated into the specification as if it were individually recited herein. For example, if a range of 1 to 10 is described, that range includes all values therebetween, such as for example, 1.1, 2.5, 3.335, 5, 6.179, 8.9999, etc., and includes all sub-ranges therebetween, such as for example, 1 to 3.65, 2.8 to 8.14, 1.93 to 9, etc., even if those specific values or specific sub-ranges are not explicitly stated.

When any phrase (i.e., one or more words) appearing in a claim is followed by a drawing element number, that drawing element number is exemplary and non-limiting on claim scope.

No claim of this document is intended to invoke 35 USC 112(f) unless the precise phrase "means for" is followed by a gerund.

Any information in any material (e.g., a United States patent, United States patent application, book, article, web page, etc.) that has been incorporated by reference herein, is incorporated by reference herein in its entirety to its fullest enabling extent permitted by law yet only to the extent that no conflict exists between such information and the other definitions, statements, and/or drawings set forth herein. In the event of such conflict, including a conflict that would render invalid any claim herein or seeking priority hereto, then any such conflicting information in such material is specifically not incorporated by reference herein. Any specific information in any portion of any material that has been incorporated by reference herein that identifies, criticizes, or compares to any prior art is not incorporated by reference herein.

Applicant intends that each claim presented herein and at any point during the prosecution of this application, and in any application that claims priority hereto, defines a distinct patentable invention and that the scope of that invention must change commensurately if and as the scope of that claim changes during its prosecution. Thus, within this document, and during prosecution of any patent application related hereto, any reference to any claimed subject matter is intended to reference the precise language of the then-pending claimed subject matter at that particular point in time only.

Accordingly, every portion (e.g., title, field, background, summary, description, abstract, drawing figure, etc.) of this document, other than the claims themselves and any provided definitions of the phrases used therein, is to be regarded as illustrative in nature, and not as restrictive. The scope of subject matter protected by any claim of any patent that issues based on this document is defined and limited only by the precise language of that claim (and all legal equivalents thereof) and any provided definition of any phrase used in that claim, as informed by the context of this document.

What is claimed is:

1. A flowmeter-free indirect calorimetry system configured to facilitate determination of the oxygen consumption, carbon dioxide production, respiratory exchange ratio, and/or energy expenditure of a mammal, the system comprising:
   a mixing tank configured to contain a mixture comprising at least a portion of each of a group of samples of exhaled gases provided by the mammal during a predetermined time period;
   a flow tube configured to route each of the group of samples toward the mixing tank;
   a conduit configured to convey the exhaled gases from the flow tube toward the mixing tank and configured to reduce the water vapor pressure of the exhaled gases within the conduit to approximately a water vapor pressure in air outside the conduit;
   a plurality of sensors comprising:
   an oxygen sensor configured to measure a volumetric oxygen fraction of the mixture in the mixing tank;
   a self-calibrating carbon dioxide sensor configured to measure a volumetric carbon dioxide fraction of the mixture in the mixing tank;
   a relative humidity sensor configured to measure a relative humidity of the mixture in the mixing tank;
   a temperature sensor configured to measure a temperature of the mixture in the mixing tank; and
   a barometric pressure sensor configured to measure a barometric pressure of the mixture in the mixing tank;
   a one-way inlet valve configured to prevent the mixture from escaping from the tank via the conduit;
   a wireless transceiver configured to convey sensor measurement data; and
   a battery configured to power the sensors and/or the wireless transceiver;
   wherein:
   the tank is formed from a non-conductive plastic;
   the tank comprises a removable lid and a gasket configured to form a gas-tight seal between the tank and the lid;
   the tank is configured to promote homogeneous mixing of the samples;
   the tank comprises an inlet port and an outlet port, an entrance to the inlet port aligned perpendicularly to an entrance to the outlet port;
   the battery is located on a bottom of the tank;
   the barometric pressure sensor is integrated with the oxygen sensor;
   the temperature sensor is integrated with the carbon dioxide sensor; and
   the relative humidity sensor is integrated with the carbon dioxide sensor.

2. A flowmeter-free indirect calorimetry method that is configured to facilitate determination of the oxygen consumption, carbon dioxide production, respiratory exchange ratio, and/or energy expenditure of a mammal, the method comprising activities comprising:
   sampling at least a portion of each of a group of samples of exhaled gases provided by the mammal during a predetermined time period, the sampler configured to direct each of the group of samples toward a mixing tank;
   conveying the samples through a conduit from the flow tube toward the mixing tank, the conduit configured to reduce the water vapor pressure of the exhaled gases within the conduit to approximately a water vapor pressure in air outside the conduit;
   in the mixing tank, mix the samples to form a mixture;

via an oxygen sensor, measuring a volumetric oxygen fraction of the mixture in the mixing tank;

via a self-calibrating carbon dioxide sensor, measuring a volumetric carbon dioxide fraction of the mixture in the mixing tank;

measuring a relative humidity of the mixture in the mixing tank;

measuring a temperature of the mixture in the mixing tank;

measuring a barometric pressure of the mixture in the mixing tank;

prior to the mixing tank containing the mixture, and via the oxygen sensor, measuring a volumetric oxygen fraction of a gaseous content of the tank;

prior to the mixing tank containing the mixture, and via the carbon dioxide sensor, measuring a volumetric carbon dioxide fraction of the gaseous content of the tank;

wirelessly transmitting sensor measurement data for determination of the oxygen consumption, carbon dioxide production, respiratory exchange ratio, and/or energy expenditure based on the volumetric oxygen fraction and the volumetric carbon dioxide fraction;

wirelessly transmitting the volumetric oxygen fraction;

wirelessly transmitting the volumetric carbon dioxide fraction;

wirelessly transmitting the relative humidity;

wirelessly transmitting the temperature;

wirelessly transmitting the barometric pressure;

determining the oxygen consumption, carbon dioxide production, respiratory exchange ratio, and/or energy expenditure based on the volumetric oxygen fraction and the volumetric carbon dioxide fraction;

wherein:

the determined oxygen consumption, carbon dioxide production, respiratory exchange ratio, and/or energy expenditure is substantially independent of a time constant of the oxygen sensor and a time constant of the carbon dioxide sensor;

a pressure in the tank remains at substantially atmospheric pressure throughout said measuring activities.

3. The system of claim 1, further comprising:

a vacuum pump configured to induce flow of the exhaled gases to the tank via the flow tube.

4. The method of claim 2, further comprising:

inducing flow of the samples to the tank via a vacuum pump.

\* \* \* \* \*